(12) United States Patent
Wendlandt

(10) Patent No.: US 8,602,973 B2
(45) Date of Patent: Dec. 10, 2013

(54) CATHETER INTRODUCER SYSTEM FOR EXPLORATION OF BODY CAVITIES

(75) Inventor: Jeffrey Michael Wendlandt, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 356 days.

(21) Appl. No.: 12/567,376

(22) Filed: Sep. 25, 2009

(65) Prior Publication Data

US 2010/0016665 A1    Jan. 21, 2010

Related U.S. Application Data

(63) Continuation of application No. 11/429,281, filed on Jun. 26, 2006, now Pat. No. 7,699,771, which is a continuation of application No. 10/282,211, filed on Oct. 29, 2002, now Pat. No. 7,066,880, which is a continuation of application No. 09/492,448, filed on Jan. 27, 2000, now Pat. No. 6,517,477.

(51) Int. Cl.
*A61B 1/01* (2006.01)
*A61B 1/00* (2006.01)

(52) U.S. Cl.
CPC .......... *A61B 1/00156* (2013.01); *A61B 1/00094* (2013.01); *A61B 1/00082* (2013.01); *A61B 1/01* (2013.01)
USPC ............................ 600/114; 600/139; 600/146

(58) Field of Classification Search
USPC ................. 600/114–116, 146, 152, 156, 139; 606/108; 604/95.01, 95.03, 103.03, 604/176–178
See application file for complete search history.

(56) References Cited

U.S. PATENT DOCUMENTS

| 2,767,705 A | 10/1956 | Moore |
| 3,168,092 A | 2/1965 | Silverman |
| 3,589,356 A | 6/1971 | Silverman |
| 3,665,928 A | 5/1972 | Del Guercio |
| 3,669,099 A | 6/1972 | Silverman |

(Continued)

FOREIGN PATENT DOCUMENTS

| DE | 19815598 A1 | 10/1999 |
| FR | 1278965 A | 12/1961 |

(Continued)

OTHER PUBLICATIONS

European Application No. 00983794.9-2319, Sep. 12, 2008 Office Action.

(Continued)

*Primary Examiner* — John P Leubecker
(74) *Attorney, Agent, or Firm* — Bookoff McAndrews, PLLC

(57) ABSTRACT

A catheter introducer system for endoscopy includes a steering section and a propulsion section located near the end of the catheter that is introduced in a body cavity. The propulsion section is designed to pull the rest of the catheter inside the body cavity, so there is no need to push the catheter along. The propulsion section includes a distal and proximal gripper portion, each of which includes a suction ring extending circumferentially around the catheter. Each suction ring can include a plurality of suction holes disposed either on a recessed portion of the suction ring or on a portion surrounded by a peripheral ridge extending above the outer surface of the suction ring. The suction ring can also include an inflatable member for urging tissue against the perimeter of the suction holes.

20 Claims, 22 Drawing Sheets

(56) References Cited

U.S. PATENT DOCUMENTS

| | | |
|---|---|---|
| 3,895,637 A | 7/1975 | Choy |
| 4,066,070 A | 1/1978 | Utsugi |
| 4,066,071 A | 1/1978 | Nagel |
| 4,148,307 A | 4/1979 | Utsugi |
| 4,176,662 A | 12/1979 | Frazer |
| 4,207,872 A | 6/1980 | Meiri et al. |
| 4,254,762 A | 3/1981 | Yoon |
| 4,321,915 A | 3/1982 | Leighton et al. |
| 4,389,208 A | 6/1983 | LeVeen et al. |
| 4,447,227 A | 5/1984 | Kotsanis |
| 4,475,902 A | 10/1984 | Schubert |
| 4,530,698 A | 7/1985 | Goldstein et al. |
| 4,615,331 A | 10/1986 | Kramann |
| 4,646,722 A | 3/1987 | Silverstein et al. |
| 4,676,228 A | 6/1987 | Krasner et al. |
| 4,676,229 A | 6/1987 | Krasnicki et al. |
| 4,690,131 A | 9/1987 | Lyddy, Jr. et al. |
| 4,735,501 A | 4/1988 | Ginsburgh et al. |
| 4,790,624 A | 12/1988 | Van Hoye et al. |
| 4,838,859 A | 6/1989 | Strassmann |
| 4,869,238 A | 9/1989 | Opie et al. |
| 4,934,786 A | 6/1990 | Krauter |
| 5,045,070 A | 9/1991 | Grodecki et al. |
| 5,051,824 A | 9/1991 | Nishigaki |
| 5,144,848 A | 9/1992 | Uenishi et al. |
| 5,163,927 A | 11/1992 | Woker et al. |
| 5,167,901 A | 12/1992 | Driver et al. |
| 5,171,305 A | 12/1992 | Schickling et al. |
| 5,179,934 A | 1/1993 | Nagayoshi et al. |
| 5,181,452 A | 1/1993 | Immega |
| 5,236,423 A | 8/1993 | Mix et al. |
| 5,243,967 A | 9/1993 | Hibino |
| 5,259,364 A | 11/1993 | Bob et al. |
| 5,259,366 A | 11/1993 | Reydel et al. |
| 5,317,952 A | 6/1994 | Immega |
| 5,325,845 A | 7/1994 | Adair |
| 5,337,732 A | 8/1994 | Grundfest et al. |
| 5,345,925 A | 9/1994 | Allred, III et al. |
| 5,364,345 A | 11/1994 | Lowery et al. |
| 5,364,353 A | 11/1994 | Corfitsen et al. |
| 5,389,100 A | 2/1995 | Bacich et al. |
| 5,398,670 A | 3/1995 | Ortiz et al. |
| 5,454,364 A | 10/1995 | Kruger |
| 5,520,222 A | 5/1996 | Chikama |
| 5,531,664 A | 7/1996 | Adachi et al. |
| 5,562,601 A | 10/1996 | Takada |
| 5,571,114 A | 11/1996 | Devanaboyina |
| 5,586,968 A | 12/1996 | Grundl et al. |
| 5,595,565 A | 1/1997 | Treat et al. |
| 5,613,947 A | 3/1997 | Chin |
| 5,662,587 A | 9/1997 | Grundfest et al. |
| 5,817,057 A | 10/1998 | Berenstein et al. |
| 5,885,209 A | 3/1999 | Green |
| 5,906,591 A | 5/1999 | Dario et al. |
| 5,941,815 A | 8/1999 | Chang |
| 5,993,427 A | 11/1999 | Rolland et al. |
| 6,007,482 A | 12/1999 | Madni et al. |
| 6,013,024 A | 1/2000 | Mitsuda et al. |
| 6,025,044 A | 2/2000 | Campbell et al. |
| 6,071,234 A | 6/2000 | Takada |
| 6,077,219 A | 6/2000 | Viebach et al. |
| 6,162,171 A | 12/2000 | Ng et al. |
| 6,358,199 B1 | 3/2002 | Pauker et al. |
| 6,416,692 B1 | 7/2002 | Iwasaki-Higbee |
| 6,485,409 B1 | 11/2002 | Voloshin et al. |
| 6,855,107 B2 * | 2/2005 | Avni et al. ............. 600/114 |
| 2002/0107478 A1 | 8/2002 | Wendlandt |

FOREIGN PATENT DOCUMENTS

| | | |
|---|---|---|
| JP | 5-433114 | 6/1993 |
| JP | 07-008447 | 1/1995 |
| WO | 99/33392 | 7/1999 |
| WO | 99/53827 | 10/1999 |
| WO | 00/44275 | 8/2000 |
| WO | 01/54565 | 8/2001 |

OTHER PUBLICATIONS

European Application No. 00983794.9-2319, Jan. 13, 2009 Interview Summary.
Japanese Office Action mailed Aug. 20, 2010 in Japanese Application No. 2001-555546 (3 pgs).
English translation of Japanese Office Action mailed Aug. 20, 2010 in Japanese Application No. 2001-555546 (4 pgs).

* cited by examiner

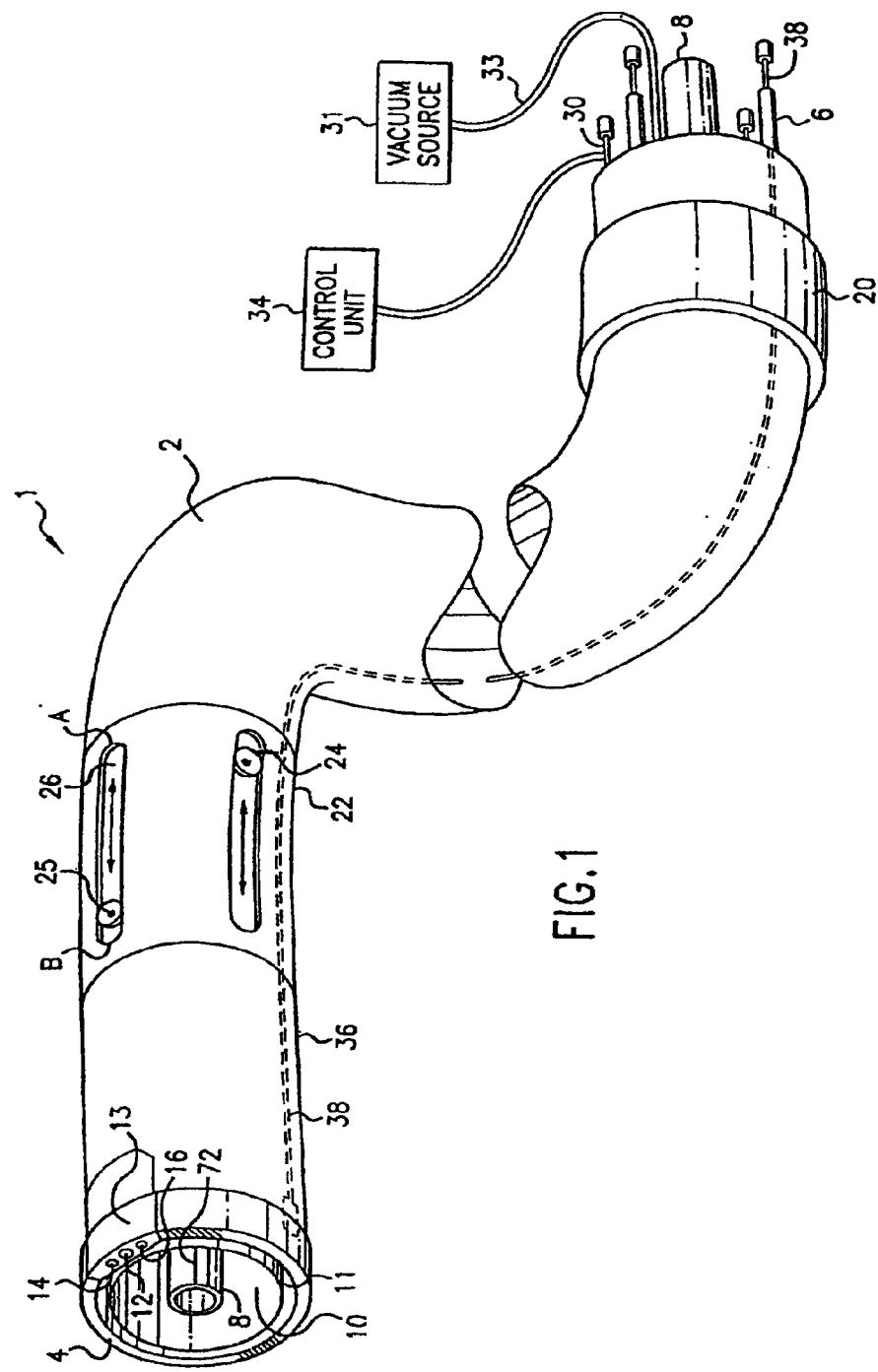

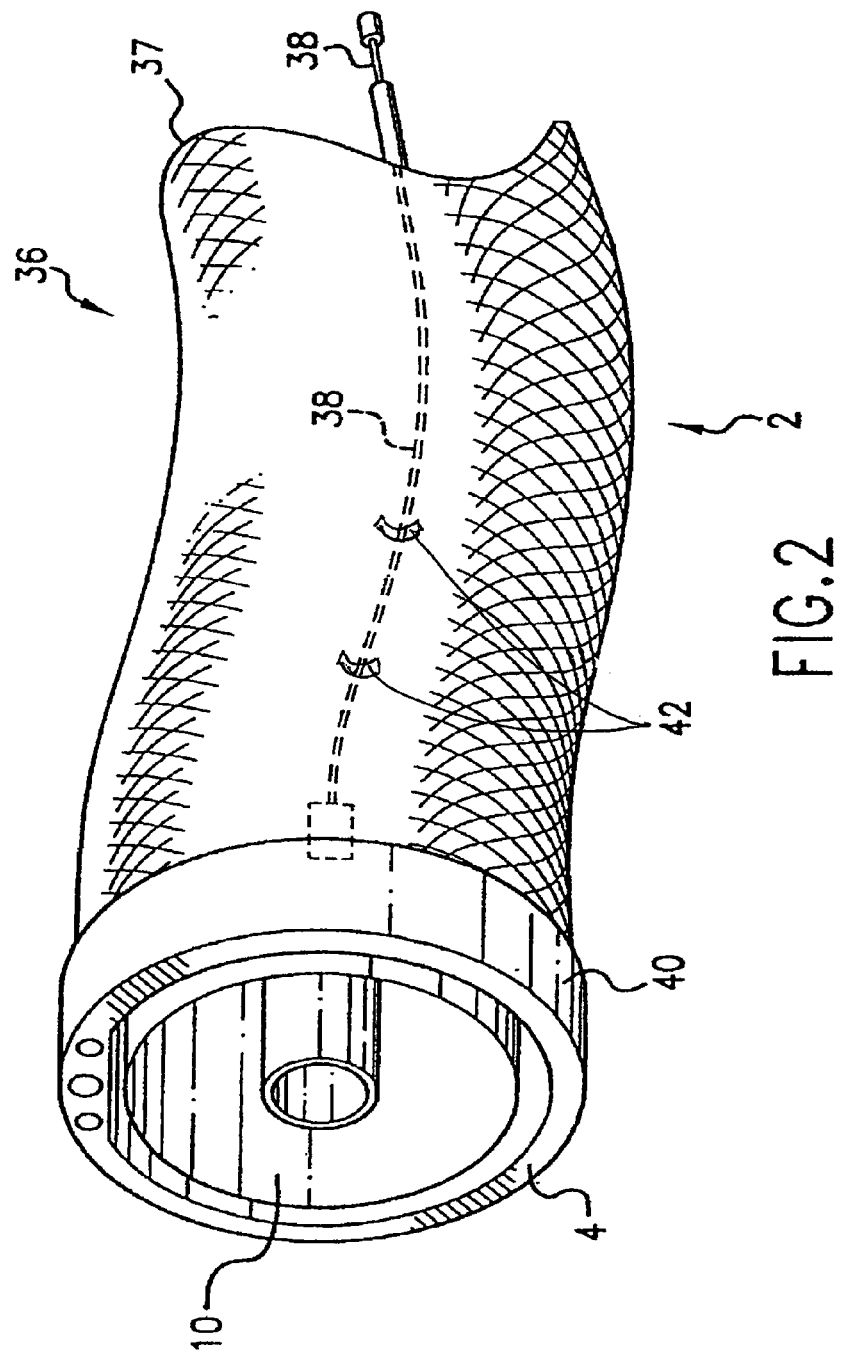

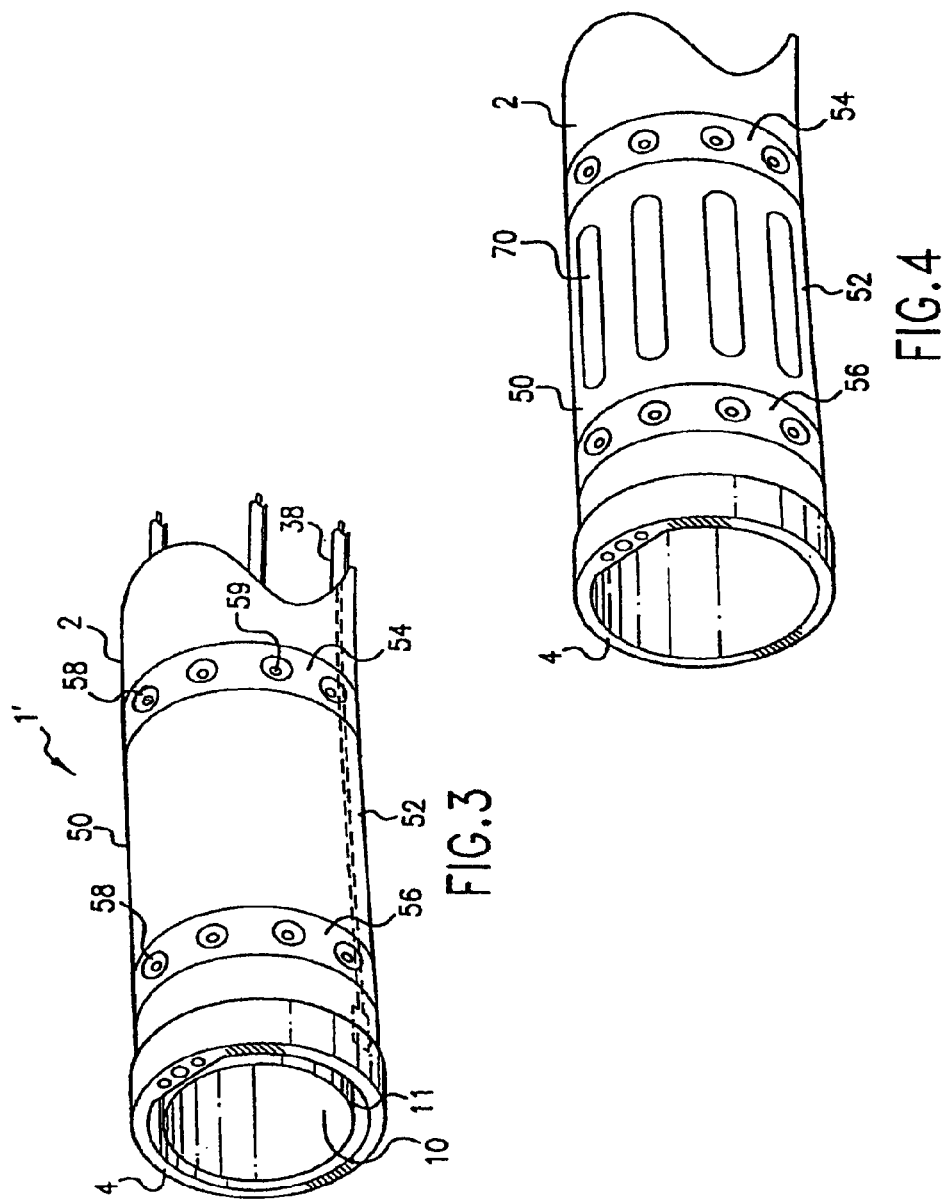

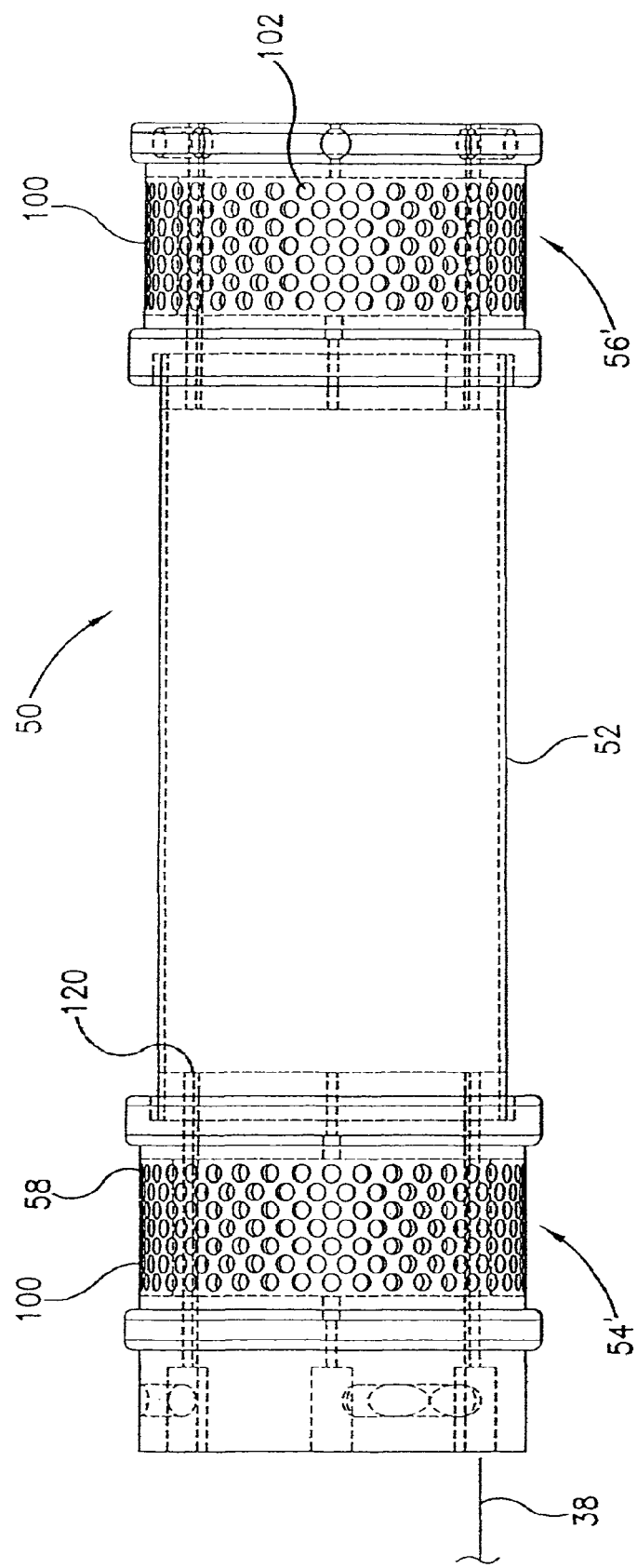

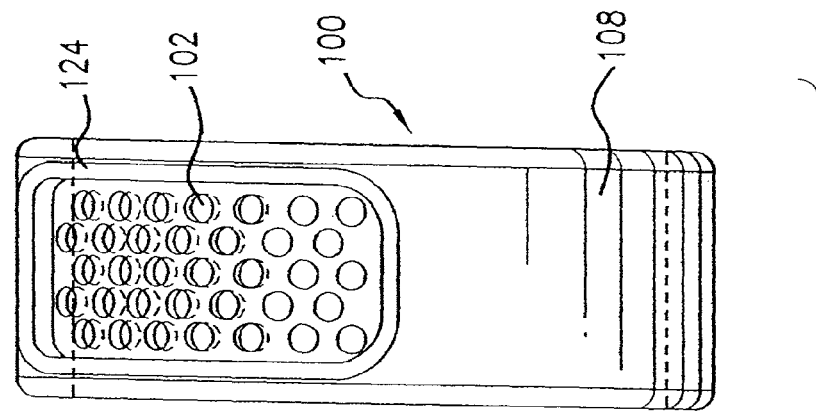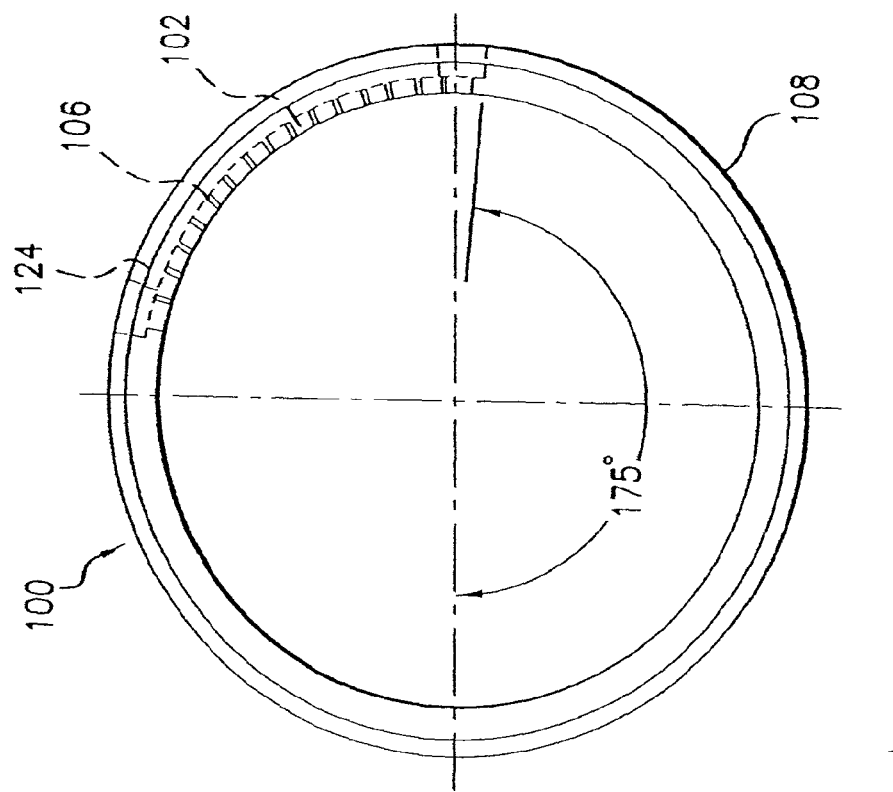
FIG. 13

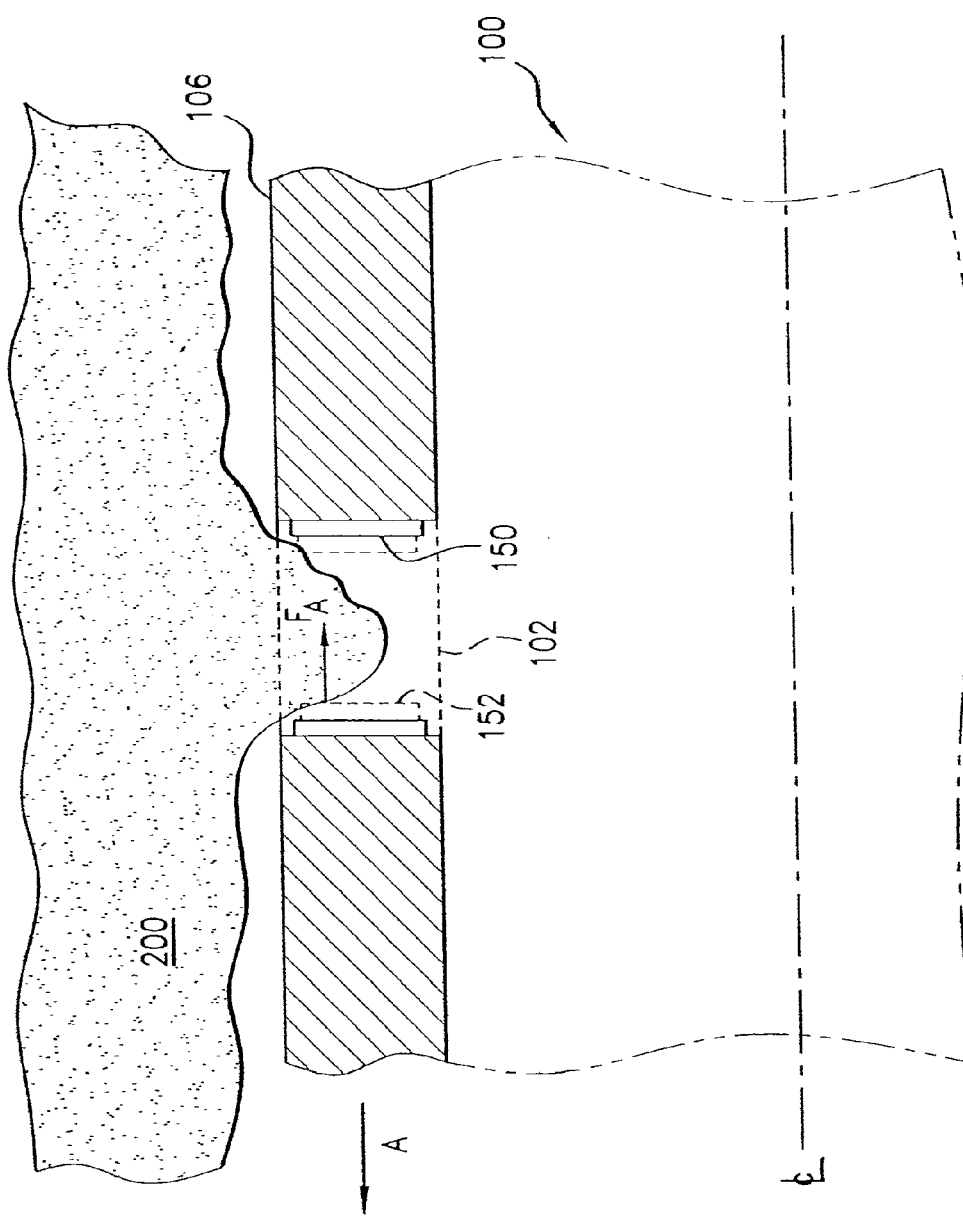

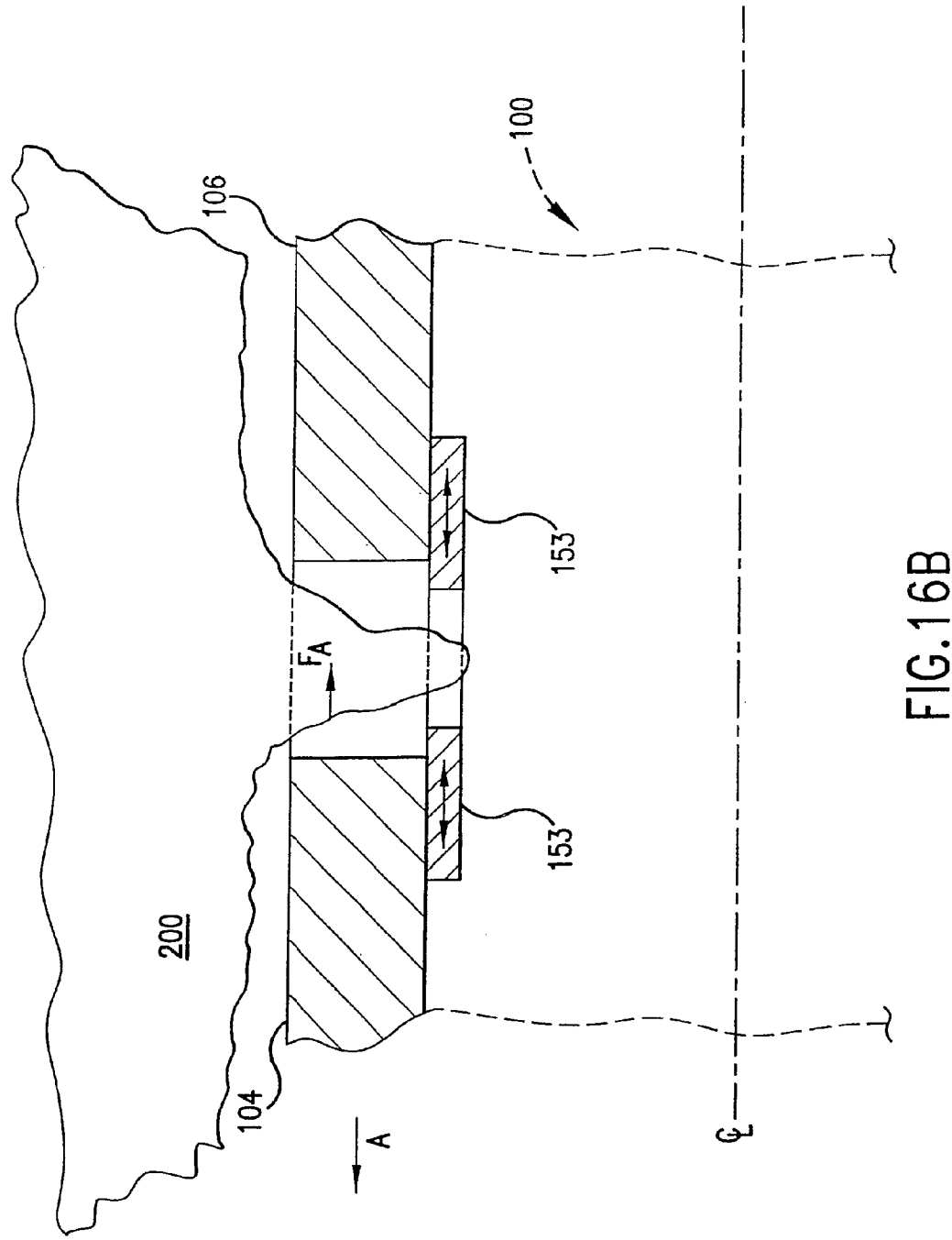

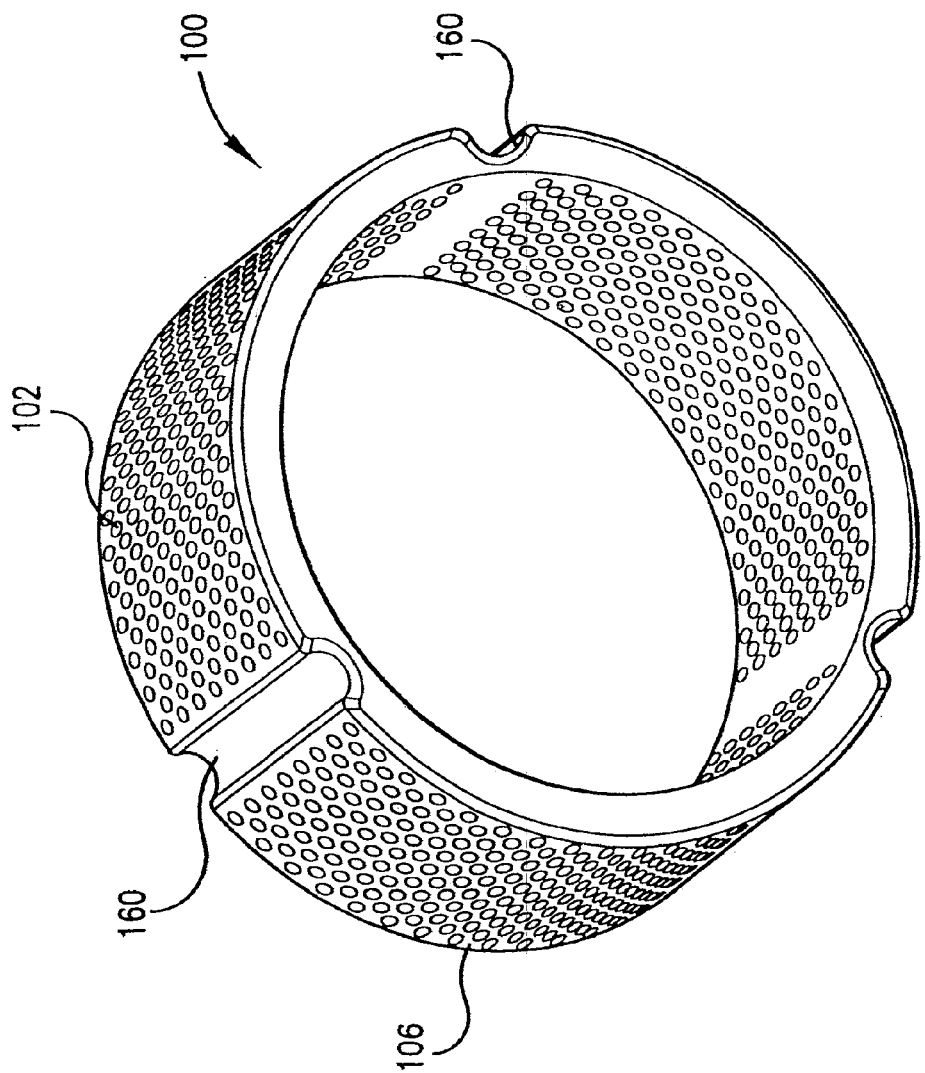

CATHETER INTRODUCER SYSTEM FOR EXPLORATION OF BODY CAVITIES

RELATED APPLICATIONS

This is a Continuation of U.S. patent application Ser. No. 11/429,281, filed Jun. 26, 2006, now U.S. Pat. No. 7,699,771, which is a Continuation of U.S. patent application Ser. No. 10/282,211, filed Oct. 29, 2002, now U.S. Pat. No. 7,066,880, which is a continuation of U.S. patent application No. 09/492,448, filed on Jan. 27, 2000, now U.S. Pat. No. 6,517,477.

BACKGROUND OF THE INVENTION

The present invention relates to a method and a device for performing endoscopy through a catheter introducer system. In particular, the present invention relates to a catheter introducer system for endoscopy designed to reach the cecum portion of the gastrointestinal tract.

DESCRIPTION OF RELATED ART

Endoscopy has become an increasingly important tool in diagnosing and in treating ailments of the gastrointestinal tract, also referred to as the GI tract. Typical endoscopes are essentially formed by a somewhat flexible tube that is pushed through the GI tract, after being introduced in the body cavity starting from the rectum or starting from the esophagus. The endoscope has a steerable tip to facilitate navigation through the GI tract, and typically has to be sufficiently stiff so that it can be pushed further along the body cavity. The tip of the endoscope that is introduced in the GI tract can be outfitted with several devices, most notably an illumination device and a vision device, such as a vision integrated circuit, so that the operator of the endoscope can observe the interior of the GI tract and maneuver the endoscope in the proper position.

Once the endoscope is in position, other tools attached to the endoscope or inserted through the endoscope can be brought to the proper position in the GI tract. Various procedures can then be carried out, such as removing polyps, performing sutures, irrigation, suction, and removing other tissues. The various tools that are used together with the endoscope can be either inserted separately in the GI tract and placed in the proper position independently, or may travel in a working channel of the endoscope, so that once the endoscope is positioned at the desired location in the GI tract, the tools inserted in the endoscope will also easily reach that position.

Endoscopes or other smaller similar devices can also be used to explore other body cavities, for example airways or blood vessels. These probes must be small to fit in the smaller cavities, and care must be taken to avoid damage to the more fragile membranes lining these cavities.

Current state of the art endoscopes are very capable devices, and endoscopy has been very successful in diagnostic and therapeutic applications with the use of current endoscopes and the current arsenal of tools that can be inserted through the working channel of the endoscope, or can be attached to the outside of the endoscope. However, current endoscope technology has limitations and drawbacks. One of the greatest drawbacks of current endoscopes is that the working channel is small relative to overall diameter of the endoscope, and is further limited by the space taken up by vision, irrigation, suction, light, and control cabling mechanisms that are part of the endoscope and are required to control the endoscope. Thus there is a very small area left for other tools to be introduced through the endoscope.

Current endoscopes are also difficult to maneuver, particularly when the endoscope has to be pushed all the way to a far portion of the intestine, such as the cecum, located at the beginning portion of the large intestine. Currently, reaching the cecum requires training, skill, luck and trial and error on the part of the operator. Current endoscopes have to be maneuvered by pushing them inside the gastrointestinal tract, while steering the far end inside the body cavity. This situation creates an inherently unstable condition, where a long tube is being pushed through a narrow cavity. This requires the endoscope tube to be rather rigid, resulting in discomfort to the patient as the endoscope is maneuvered. Because of this, the patient often must be sedated.

Once the cecum has been reached, additional tools still have to be navigated through the body to reach the location, and if the endoscope is withdrawn from that location to make room for other tools, access has to be reestablished using the same complicated procedure. Current endoscopes tend to be reusable because of the high cost of their components, and thus require thorough cleaning to sterilize them. Sterilization can be difficult to guarantee, and in many instances a disposable device would be preferable.

Accordingly, there is a need for an improved type of endoscope with a introducer system that obviates some of the drawbacks of currently known endoscopes.

SUMMARY OF THE INVENTION

The present invention is directed to a catheter introducer system for endoscopy that substantially obviates one or more of the problems due to limitations and disadvantages of the related art, and that can be used more easily and with less discomfort to the patient. Additional features and advantages of the invention will be set forth in the description which follows, and in part will be apparent from the description, or may be learned by practice of the invention. Other advantages of the invention will be realized and obtained by the apparatus and method particularly pointed out in the written description and claims hereof, as well as the appended drawings.

To achieve these and other advantages and in accordance with the purpose of the invention, as embodied and broadly described, the invention is a catheter introducer system for endoscopy tools, which includes a flexible tubular catheter defining a working channel and having a distal end for introduction in a body cavity and a proximal end opposite to the distal end. The introducer system also includes a propulsion section disposed adjacent to the distal end of the catheter and adapted for pulling the catheter through the cavity, as well as a steering section disposed adjacent to the distal end of the catheter and adapted for pointing the distal end in a desired direction. Control means for commanding the operation of the propulsion section and of the steering section are also provided. The proximal end of the catheter has an opening to introduce endoscopy tools in the catheter. The distal end can be tapered, and has another opening to allow the endoscopy tools to exit the catheter and be used within the body cavity. A tool positioning system can also be included in the distal end of the catheter to position the endoscopy tools. A rigid sheath can be used at the entrance of the body cavity to surround the flexible catheter and prevent interference or binding of the flexible catheter at the entrance point of the cavity.

In another aspect, the invention is a method for navigating a catheter introducer for endoscopy in a body cavity by introducing a distal end of the catheter containing a propulsion section into the body cavity, attaching a distal gripper portion of the propulsion section to an inner surface of the body cavity, and reducing a distance between the distal gripper portion and a proximate gripper portion of the propulsion section, the proximate gripper portion being disposed further from the distal end than the distal gripper portion. The next steps include attaching the proximate gripper portion and releasing the distal gripper portion from the inner surface, and increasing the distance between the distal and the proximate gripper portions to extend the distal end further in the body cavity.

In a further aspect, the invention is a method for navigating a catheter introducer for endoscopy in a body cavity that includes introducing a distal end of the catheter containing a propulsion section into the body cavity, disposing a first set of gripping pads of the propulsion section along a rear circumferential position of the catheter, and attaching the first set of gripping pads to an inner surface of the body cavity. This is followed by disposing a second set of gripping pads of the propulsion section along a front circumferential position, closer to the distal end than the rear circumferential position, attaching the second set of gripping pads to the inner surface, and releasing the first set of gripping pads from the inner surface. The process is completed by moving the second set of gripping pads substantially to the rear circumferential position and then releasing the second set of gripping pads from the inner surface.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention and are incorporated in and constitute part of the specification, illustrate several embodiments of the invention and together with the description serve to explain the present invention. In the drawings:

FIG. 1 illustrates a first embodiment of the catheter introducer system for endoscopy according to the invention;

FIG. 2 illustrates a detail of the distal end of the catheter shown in FIG. 1;

FIG. 3 illustrates a portion of a second embodiment of the catheter introducer system according to the invention;

FIG. 4 illustrates a portion of another embodiment of the catheter introducer system according to the invention;

FIG. 5 is a side elevation showing one embodiment of a steering/propulsion section according to the invention;

FIG. 13 is a front and side view of a seventh embodiment of a suction ring according to the invention;

FIG. 16 is a diagram showing the interaction of body tissue with a suction hole according to one embodiment of the invention;

FIG. 16b is a diagram showing the interaction of body tissue with a suction hole according to another embodiment of the invention;

FIG. 20 is a perspective view of a twelfth embodiment of a suction ring according to the invention.

DETAILED DESCRIPTION OF THE INVENTION

Figure 1A:
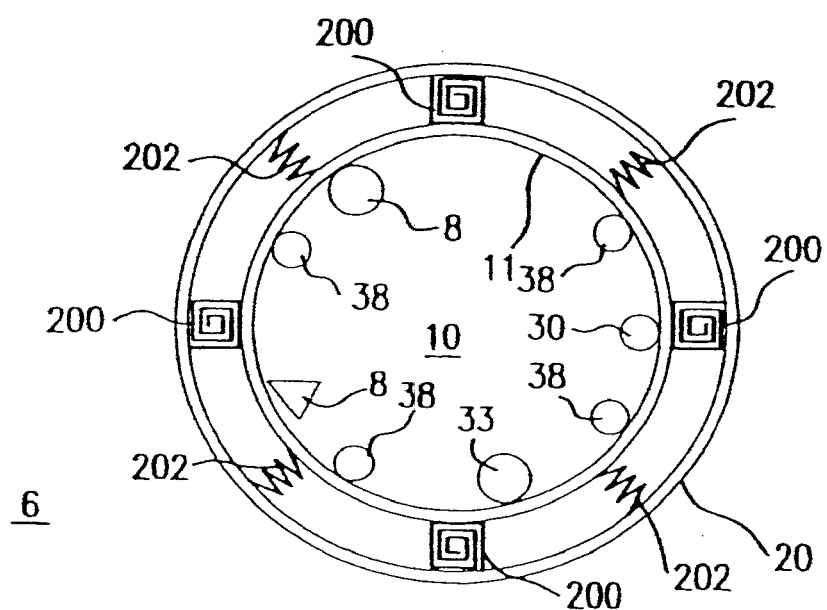
FIG. 1a illustrates a detail of the proximal end of the catheter shown in FIG. 1.

The catheter introducer system according to the present invention consists of a large catheter having an outer diameter that is customized to fit within the portion of body cavity into which it is to operate, for example the colon, esophagus, or other part of the GI tract. The catheter may be customized to the size of body cavities of individual patients. A steerable tip is included at the distal end of the catheter that is introduced in the body cavity, so that the device can easily travel inside the GI tract or other body cavity that is the subject of the procedure. A propulsion section is also included near the distal end of the catheter, that operates by pulling the distal end through the body cavity, so that the rest of the device is also pulled along. In this manner, a very flexible catheter tube can be used. A more flexible catheter results in less discomfort to the patient, and can thus be made of a larger diameter than a rigid catheter could be made. The patient also does not have to be sedated for this procedure.

The catheter introducer system has several functions, including navigation and maneuvering in the GI tract, providing light and vision devices to see the areas surrounding the tip of the catheter, providing suction, irrigation and tissue extraction, transporting devices for image acquisition such as optical and ultrasound sensors, and providing a working channel and tool manipulation for various endoscopy tools.

Because of the design of the catheter according to the present invention, a larger diameter tube can be used, so that a large working channel is provided for introduction and maneuvering of other tools used during endoscopic procedures. The propulsion and steering sections allow the catheter to maneuver easily in the colon, or in other parts of the GI tract, including hard to reach parts such as the cecum. Once the catheter is positioned near the area of the GI tract of interest, it can remain there while various tools are introduced through the working channel, and thus access to the affected area of the GI tract can easily be accomplished by successive and different tools. Many components of this catheter introducer system are disposable, thus obviating some of the problems due to difficult sterilization procedures.

FIG. 1 illustrates a first embodiment of the endoscopy delivery catheter according to the invention. Catheter introducer system 1 includes a flexible tubular catheter 2 having a distal end 4 and a proximal end 6. Distal end 4 is the end of the catheter that is introduced in the body cavity, while proximal end 6 is at the opposite end from distal end 4 and remains outside of the body cavity. Flexible catheter 2 is hollow on the inside, thus defining a working channel 10 that extends from proximal end 6 to distal end 4. Since the catheter 2 is very flexible, it can have a large diameter, so that a large working channel 10 is provided for introduction and maneuvering of endoscopy tools 8.

In a preferred embodiment, the working channel is defined by a sheath 11, which is non-collapsible and thus tends to maintain a circular cross section even when it is bent along its axis. Sheath 11 can also include a coil to help maintain its cross sectional shape. The working channel tends to retain a constant size when sheath 11 is used, so that binding of the tools inserted in the working channel 10 is prevented, and the outer surface of catheter 2 can be very light and flexible. For example, the working channel can have a diameter of about 14 mm, resulting in an outer diameter of the device of about 20 mm.

Various types of tools 8 can be inserted through the working channel 10, so that once catheter 2 is in position within the body cavity, additional endoscopy tools can quickly and easily reach the area of interest within the GI tract. Any present tool for endoscopy can be adapted for use in the working channel 10 of catheter 2, and the large cross section of working channel 10 opens the possibility of developing new tools and procedures that can improve the function of current devices. In a preferred embodiment, the catheter portion 2 can be disposable, so that cleanliness and sterilization of the catheter introducer system can be assured.

In addition to tools 8 that can be introduced through the catheter introducer system 1, some other devices can be built-in within catheter 2. For example, a vision chip 12 such as a charge coupled device (CCD) or a CMOS and light source 14 can be built in the catheter, as well as an accessory 16 that may perform suction, irrigation, or other functions. In addition to a vision chip 12, other sensors could be provided on the catheter introducer system 1. For example, X-ray or ultrasound sensors could be utilized.

In a preferred embodiment, vision chip 12 and light source 14 can be part of a modular vision tool 13 that can be detached from catheter 2 and replaced. For simplicity, vision tool 13 could snap in place at the front of catheter 2, so that electrical or other connections would be made automatically. Using a snap-on vision tool 13 facilitates sterilization of the device, because most components of the catheter introducer system 1 other than vision tool 13 could be made disposable. If a CCD is used in vision tool 13, only thin wires need to connect the CCD to the proximate end of the catheter 2. Catheter 2 thus remains flexible and can be manufactured cheaply. If necessary, a fluid supply could be provided to the CCD lens, to clean it of contaminants.

The catheter portion can be provided with a rectal sheath 20 made of a more rigid material and located at the entrance of the body cavity, for example to prevent the sphincter from compressing and binding the flexible catheter. Sheath 20 is designed to maintain the sphincter in an open position and allow the catheter to move back and forth freely. The sheath may also provide a seal with the outer surface of the catheter. This seal is particularly useful when air is used to inflate the colon, to facilitate the visual inspection. In a further embodiment according to the invention, an active sheath can be used to assist the motion of the catheter, by pushing and pulling on the catheter. The means to move the catheter axially and rotationally may be, for example an endless screw mechanism, rack and pinion mechanism, or axial and radial actuators of known type. FIG. 1a shows an embodiment where the sheath 20 has axial actuators 200 and radial actuators 202.

The catheter introducer system shown in FIG. 1 includes a propulsion section 22 that is located near the distal end 4 of catheter 2. The propulsion section 22 is designed to pull the portion of catheter 2 near it through a body cavity, so that the catheter 2 can easily navigate through a cavity like the GI tract. Since propulsion section 22 is designed to pull from within the body cavity, catheter 2 can be more flexible than would be possible if the catheter were pushed from outside of the body cavity, because catheter 2 does not have to transmit the compression loads caused by being pushed. As a result, this device reduces the pain and discomfort felt by the patient, because the device can be made extremely flexible in bending while also having a large diameter. Propulsion system 22 includes several sliding gripping pads 24 that can travel along guides 26 in an axial direction, along the length of the catheter 2. Gripping pads 24 are located on an outer surface of catheter 2, and in one embodiment are distributed evenly around the circumference of the catheter 2. In the preferred embodiment shown in FIG. 1, gripping pads 24 have suction ports 25 so that they can attach to the inside surface of the body cavity whenever a vacuum is applied to the suction port 25.

In a preferred embodiment according to the invention, each one of gripping pads 24 can move along guide 26 independently, and the suction applied to each of suction ports 25 can be turned on or off independently from that of the other suction ports 25. In a more preferred embodiment, four gripping pads 24 are provided in four sliding channels 26, one in each channel, and are spaced about 90° apart from each other around the circumference of catheter 2. Opposing pairs of gripping pads 24 can be coordinated to move and apply suction in unison.

During operation of the propulsion section 22, the gripping pads 24 move in coordinated manner, gripping, releasing, and sliding to move the catheter 2 forward and backward. To move forward, for example, approximately half of the pads 24 in a first group located at the first position A in sliding channel 26 apply a vacuum through suction ports 25, so that they become attached to the tissue of the body cavity. At the same time, a second group of gripping pads 24 is moved to a second position B in sliding channel 26, without vacuum being applied to their suctions ports 25. In this phase phase, air may be expelled through the moving suction ports, to ensure that body tissue does not stick to the moving gripping pads 24. This makes it easier for the gripping pads 24 to slide along the cavity wall. A saline solution or other fluid may also be expelled through suction ports 25, to remove any contaminants from the ports.

Once the second group of gripping pads 24 reaches position B, the vacuum is turned on to the ports 25 of those gripping pads, which attach to the tissue of the body cavity. Vacuum is at the same time turned off to the first group of gripping pads 24 at position A. At that point gripping pads 24 at position B are moved to position A, while maintaining the suction, so that the entire catheter 2 is pulled forward relative to the body cavity tissue by a distance substantially equal to the distance between points A and B of sliding channel 26.

To move backwards, for example, the same sequence can be carried out in reverse order, so that the group of gripping pads 24 to which a vacuum is applied are initially moved from point A to point B of the sliding channel 26, to force the catheter 2 out of the body cavity.

Vacuum can be applied to suction ports 25 by turning on and off a connection to a vacuum source 31. The sliding movement of gripping pads 24 and suction ports 25 within sliding channel 26 can be performed in a variety of manners, such as by mechanical movement of push-pull wires 30, with force from an inflating bellows, or by activation of linear actuators that respond to electricity or other changes in their operating environment. Movement of gripping pads 24 within sliding channel 26 can also be accomplished in other known manners, such as by using shape memory actuators, piezoelectric actuators, or other types of actuators commonly known as artificial muscles.

The application of a vacuum to the various suction ports 25, movement of gripping pads 24 within sliding channels 26, and other control functions can be performed by hand or, in a preferred embodiment, by a control unit 34 that automatically coordinates the movement of the individual suctions pads in the sliding channels and application of suction in response to instructions of the operator of the catheter system. The operator, for example, could select movement of the catheter in or out of the cavity, and control unit 34 could operate propulsion section 22 accordingly. Control unit 34 could include, for example, a memory containing sequences of instructions for movement and application of vacuum by the gripping pads 24, that result in desired movement of the catheter 2. Control unit 34 could also include an electronic computer to convert those sequences into commands for servo motors, valves, and other actuators that affect the operation of gripping pads 24, and control supply of vacuum from vacuum source 31 via ducts 33.

Each of gripping pads 24 could also have more than one suction port 25 applying vacuum to the body cavity tissue. A perforated surface could be used instead of an individual port, having a configuration that will be described in detail below, in the context of a perforated suction ring.

In yet another embodiment, different methods for gripping the inside of the body cavity could be used instead of the suction gripping pads 24. For example, inflatable balloons could grip the tissue of the body cavity when inflated, and could be operated in the same manner as the gripping pads with suction ports.

The catheter introducer system shown in FIG. 1 includes a steering section 36 also located adjacent to the distal end 4 of the catheter 2. In the preferred embodiment the steering section 36 is closer to the opening of the distal end 4 of the catheter than the propulsion section 22. However, the opposite arrangement can also be utilized successfully. Steering section 36 allows an operator to change the direction where distal end 4 is pointed inside the body cavity. In the preferred embodiment shown in FIG. 2, the steering section 36 comprises a flexible structure, such as a braid or mesh 37, that defines the outer circumferential surface of the tube-like catheter 2. Flexible mesh 37 can be collapsed and can also be extended to several times its collapsed length in a direction along the length of the catheter 2. In a preferred embodiment, steering section 36 is formed of a flexible mesh tube having similar properties to those of an endoscopic or vascular stent, such as, for example, the Wallstent® manufactured by Boston Scientific Corporation. The flexible mesh tube is designed to provide sufficient rigidity to maintain a tube-like shape, while also allowing a change in length of the section.

The tube formed by flexible mesh 37 can also be bent in a desired direction by stretching mesh 37 in one circumferential portion while compressing it on the opposite circumferential portion of the tube. Steering section 36 can thus be turned in a selected direction with respect to the center line of the catheter 2.

The stretching and turning of flexible mesh 37 can be carried out in a convenient manner by using push-pull cables 38, shown in FIG. 2. Push-pull cables 38 are sufficiently stiff such that they can carry a tension as well as a compression load, and are attached to tip 40 forming the distal end 4 of catheter 2. Tip 40 can preferably be made of aluminum or plastic. In a preferred example, push-pull wires 38 are made of NITINOL, which is a super-elastic alloy that resists elastic deformation leading to the formation of kinks. For disposable catheters, the wires 38 can alternatively be made of steel, or other materials that tend to regain their original shape after bending. However, NITINOL wires are preferred for applications where catheter 2 is used repeatedly.

Aluminum tip 40, flexible mesh 37, and push-pull wires 38 are all disposed on the circumference of catheter 2, so that working channel 10 is left free for introduction of endoscopy tools. Push-pull cables 38 exit the body cavity and exit from catheter 2 at the proximal end 6, and can be either manually controlled or can be controlled by the control unit 34. Control unit 34 controls the steering section 36 in a similar manner as it controls the propulsion section 22.

When push-pull wires 38 are moved together, the length of the steering section 36 changes, and the tip 40 on distal end 4 of catheter 2 is pushed further in the body cavity, or is withdrawn partially from the body cavity. If push-pull wires 38 are acted on differentially, steering section 36 can be turned in any direction relative to the length of the catheter 2. Sutures 42 can be used to attach push-pull wires 38 at discrete locations on the flexible mesh 37, to control their positioning and to support them, so they can transmit compression forces without buckling.

Devices other than sutures 42 can be used to hold push-pull wires 38 in position around steering section 36. For example, rigid rings can be fixed at axial locations along the steering section 36, and the push-pull wires 38 can be attached to the rings, or may be threaded through holes formed in the ring's outer portion. Alternatively, simple clips or loops can be used to tie push-pull wires 38 to specific points of mesh 37, so the wires can move only in the axial direction. Heat shrink, polyurethane, or other type of low friction flexible cladding can be applied on top of flexible mesh 37 and wires 38 to facilitate insertion and travel of the device within the body cavity. The use of a slippery coating for the catheter makes it easier for the propulsion section 22 to pull the catheter along the body cavity, and also reduce discomfort to the patient. The low friction coating can also be used on the inside of the cladding, to reduce friction with push-pull wires 38.

In a further embodiment according to the invention, the steering section 36 can have an outer surface formed by bellows instead of the flexible mesh 37. The bellows can be inflated or deflated to extend or contract, in a direction along the length of the catheter 2. Bellows can be also extended and contracted by operation of push-pull wires 38, connected to tip 40. In this case, the bellows are used simply as an outer cover for the mechanism of the steering section 36, similarly to mesh 37. Holes can be formed at the crests of the bellows ridges, to guide and keep in place the push-pull wires 38. The inflatable bellows actuators are further described in U.S. Pat. Nos. 5,181,452 and 5,317,952 which are hereby incorporated by reference. The inflation and deflation, or the extension of various bellows sections can be controlled either by hand or by a control unit 34. Use of the bellows allows steering section 36 to either change its length, or to change the direction where distal end 4 points, in a manner analogous to that described above.

As a further alternative to a mesh or bellows, a coil structure can be used to maintain the push-pull wires 38 in place, and to give some structural rigidity to the steering section 36. One or more coils can extend from tip 40 along the length of steering section 36, and can be connected to wires 38 with any of the methods described above.

Sheath 11 defining working channel 10 preferably can be attached to tip 40 but not to mesh 37. In this manner, mesh 37 can change length without affecting the shape of the working channel 10.

Figure 3A:
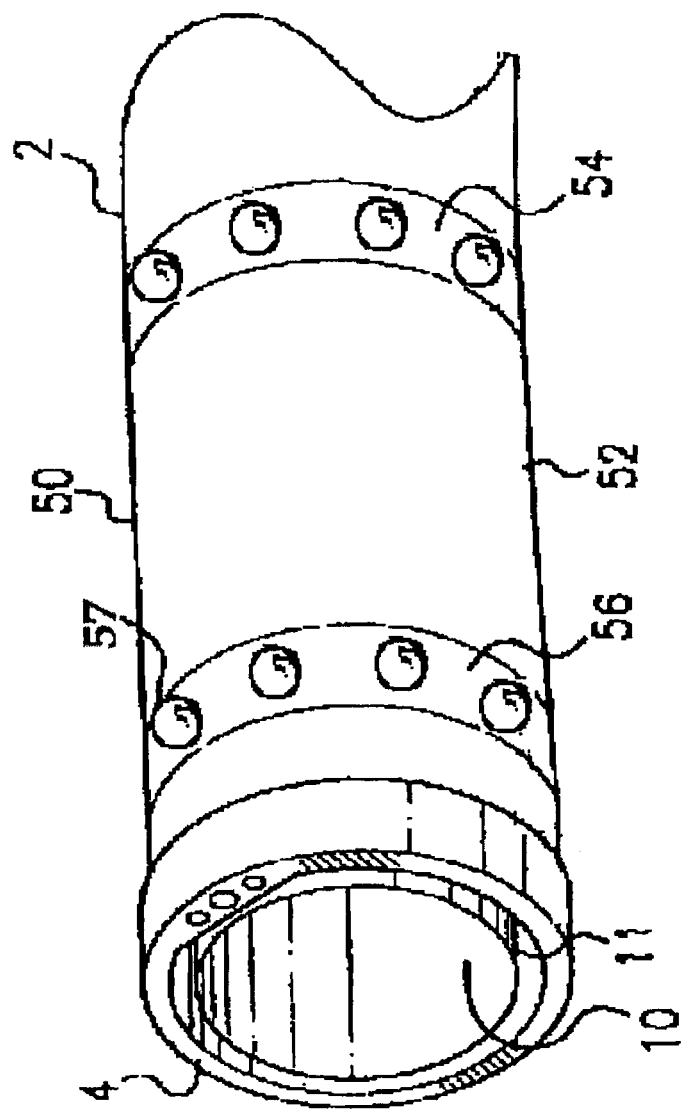
FIG. 3A illustrates a portion of another embodiment of the catheter introducer system according to the invention.

FIG. 3 shows a second embodiment of the catheter introducer system for endoscopy according to the present invention. As shown in FIG. 3, a tube-like catheter 2 defines a working channel 10 and has a distal end 4 designed for introduction in the body cavity. As described above, a resilient sheath 11 can be used to define the working channel 10. Near the distal end 4 of the catheter 2, there is a steering/propulsion section 50 that is used both to pull the rest of the catheter along in the body cavity that is being explored, and also to direct the distal end 4 of the catheter 2 in the desired direction.

Steering/propulsion section 50 comprises a steering/elongation portion 52 that provides elongation as well as steering functions for the catheter introducer system 1'. For example, steering/elongation portion 52 can be formed by a mesh with push-pull wires similar to the one described in FIG. 2. If the push-pull wires are extended or withdrawn at the same time, steering/elongation portion 52 elongates and distal end 4 of the catheter 2 is extended further or is withdrawn from the body cavity. If the push-pull wires on one side of steering/elongation portion 52 are extended, while those generally on the opposite side of the steering/elongation portion 52 are withdrawn, the steering/elongation portion 52 will turn towards the withdrawing wires, thus changing the direction in which distal end 4 is pointed. A combination of elongation and turning commands can also be given simultaneously to the steering/elongation portion 52.

In a preferred embodiment, three wires 38 are equally spaced at 120° intervals around the circumference of the steering/elongation portion 52, and can provide elongation and steering as described above.

Preferably, steering/elongation portion 52 is formed of a flexible mesh tube to which are attached push-pull wires 38. This configuration retains a large hollow working channel 10 inside the device because the integrated steering and propulsion mechanism takes up little wall thickness. Steering/propulsion section 50 also includes a proximal gripper portion 54 and a distal gripper portion 56 that are respectively positioned at the proximal and distal ends of steering/elongation portion 52. Both the proximal and distal gripper portions 54 and 56 preferably include gripping pads 58 that have suctions ports 59 that can selectively apply suction to the surrounding inner surfaces of the body cavity.

In the preferred embodiment, suction ports 59 are connected to a vacuum system with a source 31 and ducts 33, so that when the vacuum is turned on the suction port 59 will attach to the tissue of the surrounding body cavity. When the vacuum is turned off, suction port 59 releases its grip on the inner surface of the body cavity. In a different embodiment of the invention, one or both of the proximal and distal gripper portions can include other means of attaching themselves to the inner surface of the body cavity, such as inflatable balloons, suction arms, or other known devices. For example, inflatable balloons 57, as shown in F*ig*.3A, could grip tissue of the body cavity when inflated, and could be operated in the same manner as the gripping pads with suction ports.

In a different embodiment, proximal and distal gripper portions 54, 56 can include a perforated suction ring to apply vacuum to the surrounding body cavity tissue, instead of discrete gripping pads 58 with suction ports 59. Several configurations of perforated suction rings will be described below.

In another embodiment according to the invention, steering/elongation portion 52 can include, for example, inflatable bellows as described above with reference to the steering section 36, instead of push-pull wires and flexible mesh. In yet another embodiment according to the invention, the push-pull wires can be replaced by linear actuators 70 embedded within the flexible structure of catheter 2, as shown in FIG. 4 and as earlier described.

Figure 19:
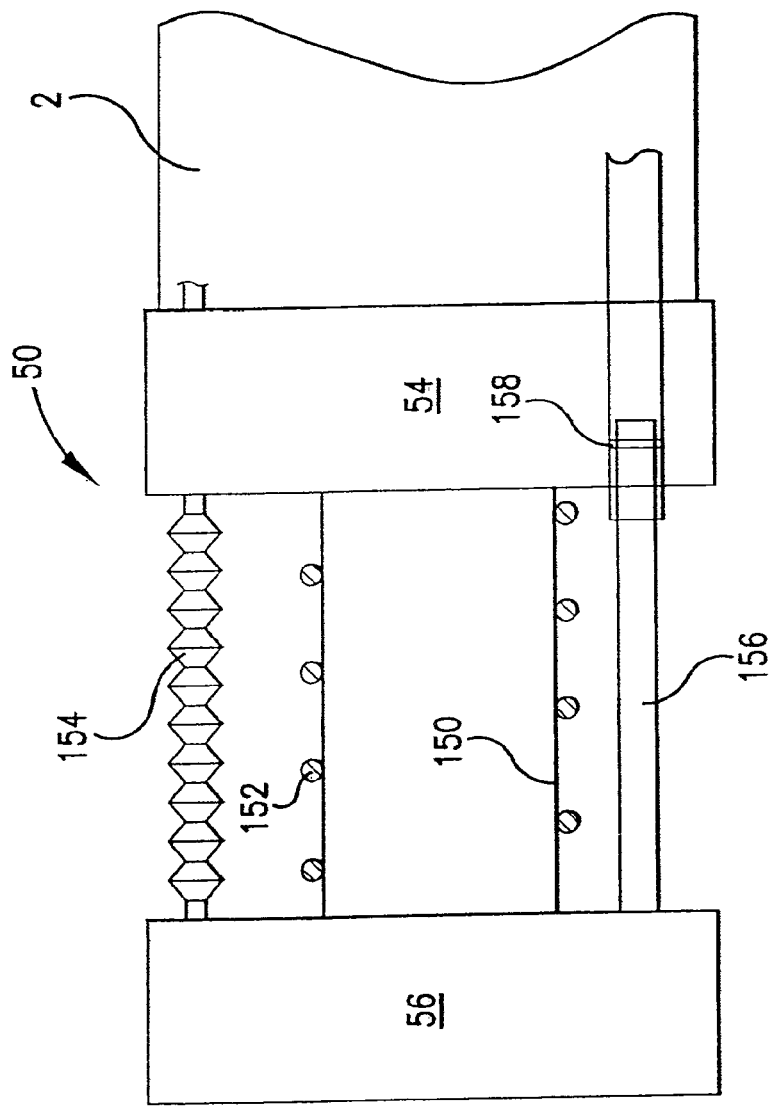
FIG. 19 is a schematic side view showing the steering/propulsion section according to one embodiment of the invention.

Gripper portions 54, 56 move alternatively closer and farther apart during the progression of catheter 2. The structures within steering/elongation portion 52 must therefore allow this movement. For example, as shown in FIG. 19, sheath 11 defining working channel 10 can be formed by a flexible membrane 150 surrounded by coils 152. This construction results in a sheath 11 that can extend and contract axially while retaining a constant cross section, and provides a smooth inner surface to the working channel 10. The tubes that provide suction to distal gripper portion 56 also have to extend and contract axially. This can be achieved, for example, using bellows shaped tubes 154, or using telescoping flexible tubes 156, with seals 158 placed between the telescoping sections.

The catheter introducer system 1' shown in FIG. 3 includes an extremely flexible catheter 2 and is designed to pull itself along the body cavity where it is introduced, rather than being pushed as is done with traditional endoscopes. The catheter moves in an inchworm fashion by coordinated motion and control of the gripper portions and of the steering/elongation portion.

For example, to move forward, the proximal gripper portion 54 attaches to the tissue of the body cavity by applying a vacuum to suction ports 59 of the proximal gripper portion 54. The steering/elongation portion 52 is then extended, so that the distal gripper portion 56 is pushed further inside the body cavity. Suction ports 59 of distal gripper portion 56 then apply a vacuum to the surrounding tissue so as to attach to the tissue, and the suction ports 59 of the proximal gripper portion 54 stop applying a vacuum. In a preferred embodiment, suction ports 59 can also eject pressurized air to completely release the surrounding tissue. At that point steering/elongation portion 52 is contracted while the distal gripper portion 56 continues to attach to the surrounding tissue, so that the portion of the catheter behind distal gripper portion 56 is pulled along inside the body cavity by a distance substantially equal to the contraction distance of steering/elongation portion 52. The process is then repeated until the distal end 4 of the catheter 2 reaches the desired position inside of the body cavity.

To move backward, the above process is reversed. For example, the proximal suction gripper 54 attaches to the tissue, while the distal gripper portion 56 releases the surrounding tissue. Steering/elongation portion 52 is contracted, so that the distal end 4 of the catheter 2 is withdrawn from the body cavity. Proximal gripper portion 54 then releases the tissue, distal gripper portion 56 attaches to the tissue and the steering/elongation portion 52 is extended, so that the portion of the catheter 2 behind distal gripper portion 56 is withdrawn from the body cavity. The order of attachment and release of grippers 54 and 56 can also be reversed, as long as the contractions and extensions of steering/elongation portion 52 cause the catheter to be respectively pulled towards or pushed away from a gripper portion 54, 56 that is attached to the tissue of the body cavity.

The catheter 2 can also simply be pulled out of the body cavity by the operator. These steps are repeated until the entirety of catheter 2 is extracted from the body cavity. Throughout the operation, steering is achieved by bending the steering/elongating portion 52 either while the insertion or extraction movement is carried out, or separately while the catheter 2 remains in position. As shown in FIG. 1, a control unit 34 can be used to coordinate the operation of steering/propulsion section 50, such as bending and elongation of steering/elongation portion 52, and application of suction.

The second embodiment according to the invention shown in FIG. 3 also provides a large working channel 10 through which various endoscopy tools can be inserted and positioned easily in the desired portion of the body cavity. A tool ideally suited for this device is a suction polypectomy device to remove polyps from the intestine. The effectiveness of such device is currently limited by the small working channel of existing endoscopes, but this drawback is resolved by using the catheter introducer system according to the invention.

Several variations can be made to the design of the gripping pads 58 and 24 described above in conjunction to the embodiments of the invention shown in FIGS. 1 and 3. These variations are designed to maximize the traction or gripping force exerted by the gripping pads on the surrounding tissue of the body cavity.

In one embodiment shown in FIG. 5, the gripping pads 58 can be replaced by a perforated suction ring 100, having an outer surface 104 with a plurality of holes 102. Independently controllable sources of suction and compressed air are provided to gripper portions 54', 56', which can be moved close together or apart along the steering/elongation portion 52, as described above with reference to FIG. 3. In this example, suction is applied to the surrounding tissue through holes 102. Holes 102 are designed to distribute the suction over a large area of tissue, so that the traction force generated is increased. A suction ring 100 with multiple holes 102 also reduces the chances that holes 102 will be clogged by the tissue, or other debris or contaminants. To further prevent clogging, provisions can be made to eject pressurized air or a liquid from holes 102, to force any contaminants out of holes 102.

Figure 6:
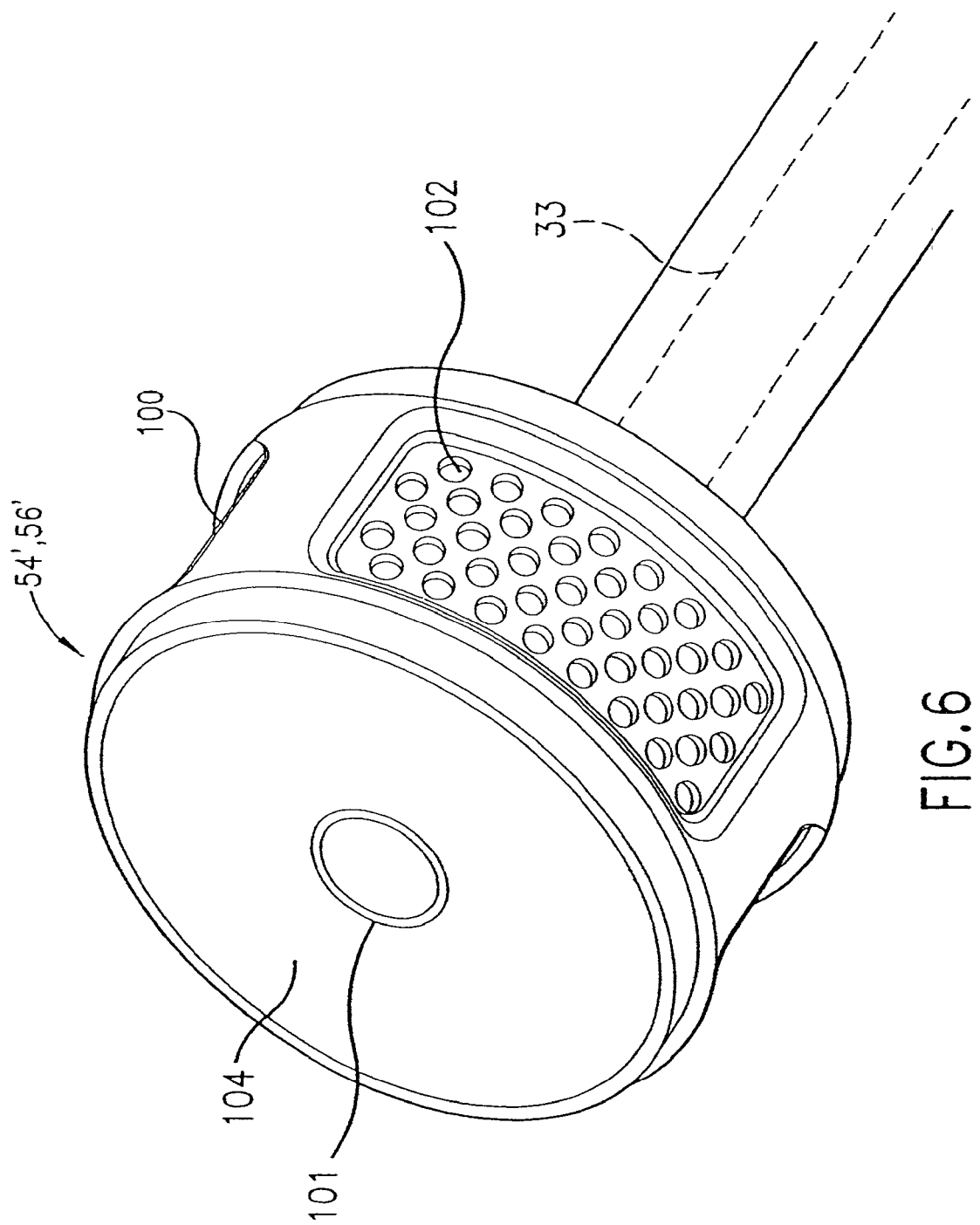
FIG. 6 is a perspective view showing a detail of one embodiment of a gripper portion.

Suction ring 100 also defines a buffer area, or plenum 101 disposed between the perforated outer surface 104 and the suction connection duct 33, as shown in FIG. 6. Plenum 101 is used to separate the suction duct 33 from the holes 102 on suction ring 100, so that suction is distributed to a larger area of tissue, and clogging of the vacuum supply is prevented. Plenum 101 can be, for example, an enclosed toroidal volume between surface 104 and the center of suction ring 100. Plenum 101 may also be divided in non-communicating portions, each connected to a different section of suction ring 100.

An additional perforated screen can be placed under the surface of suction ring 100. This additional screen has holes smaller than holes 102, and acts as a filter to further prevent clogging of duct 33. Holes 102 can have a size optimized to maximize suction, while the holes of the additional screen are optimized to stop contaminants.

The push-pull wires used to control turning and elongation of the catheter travel across at least one of the suction rings 100 before reaching the distal portion 4 of catheter 2. Thus the wires must be insulated from the suction source, to prevent vacuum leaks. For example, as shown in FIG. 5, the wires 38 could pass through a passage 120 drilled through suction ring 100, sealed from the portions connected to the suction. Alternatively, wires 38 could pass through a sealed tube crossing plenum 101.

Figure 7:
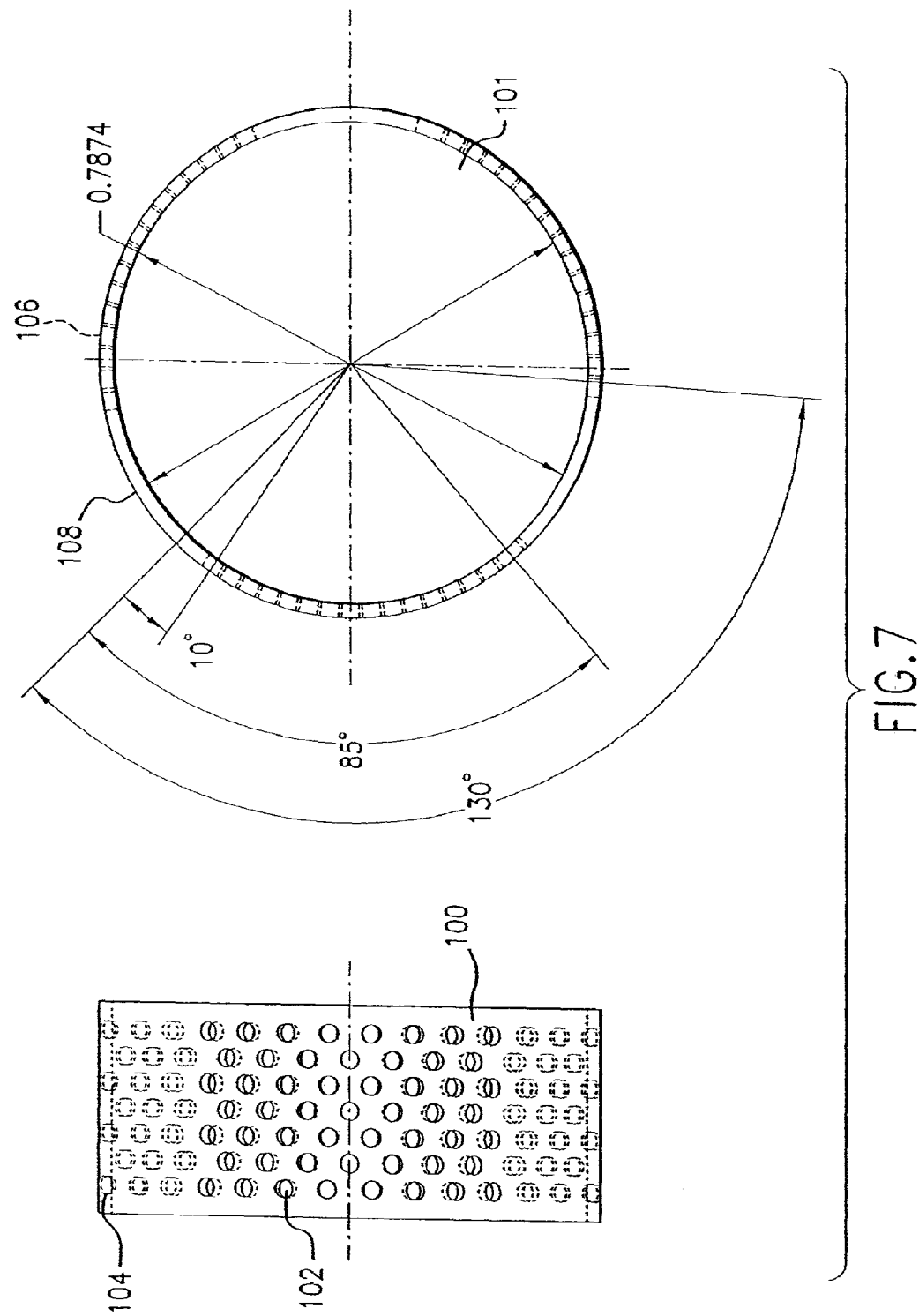
FIG. 7 is a front and side view of a first embodiment of a suction ring according to the invention.

In different embodiments, holes 102 do not have to be uniformly distributed around the outer surface 104 of perforated suction ring 100. For example, as illustrated in FIG. 7, the holes can be grouped in perforated sectors 106 separated by sectors 108 that are not perforated. Sectors 106 may be connected to separate sources of suction, so that if one of the sectors becomes detached from the tissue, the remaining sectors will not be adversely affected, and will continue to apply full suction to the portions of tissue to which they are attached. In one example, holes 102 can have a diameter of approximately 0.04 in., and sectors 106 can extend for approximately 85 degrees of arc, and can be equally spaced around the circumference of suction ring 100.

Figure 8:
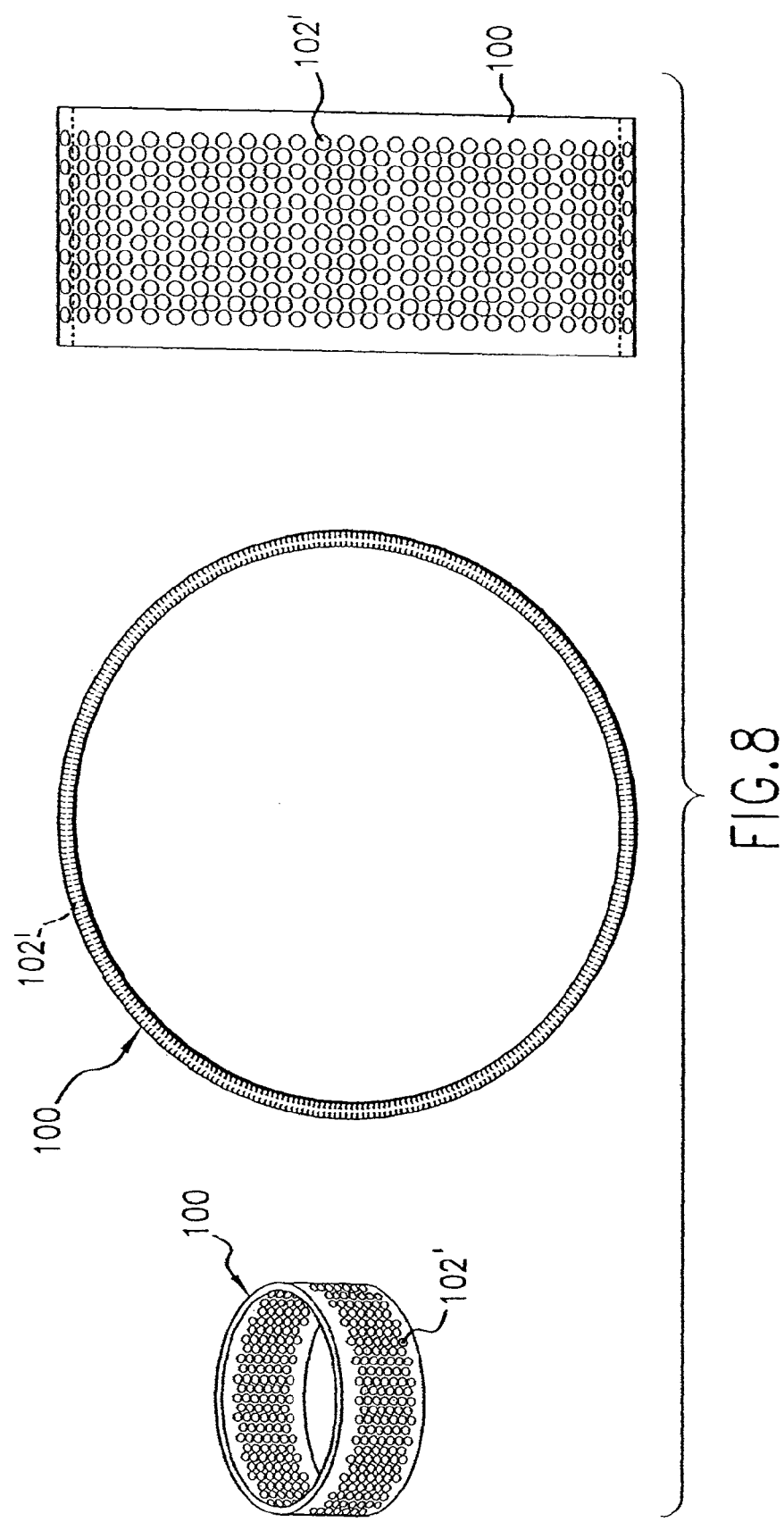
FIG. 8 is a front, perspective and side view of a second embodiment of a suction ring according to the invention.

As shown in FIG. 8, holes 102' having a different size can be utilized on suction ring 100. For example, holes of a diameter of about 0.02 in. can be formed. The size of the holes is optimized to obtain the best suction without excessive clogging. Smaller and more numerous holes tend to grip better the tissue, but clog more easily. Fewer larger holes clog less, but also tend to provide less traction on the tissue. Different sizes of holes can be used in all the configurations of suction ring 100 described here.

Figure 9:
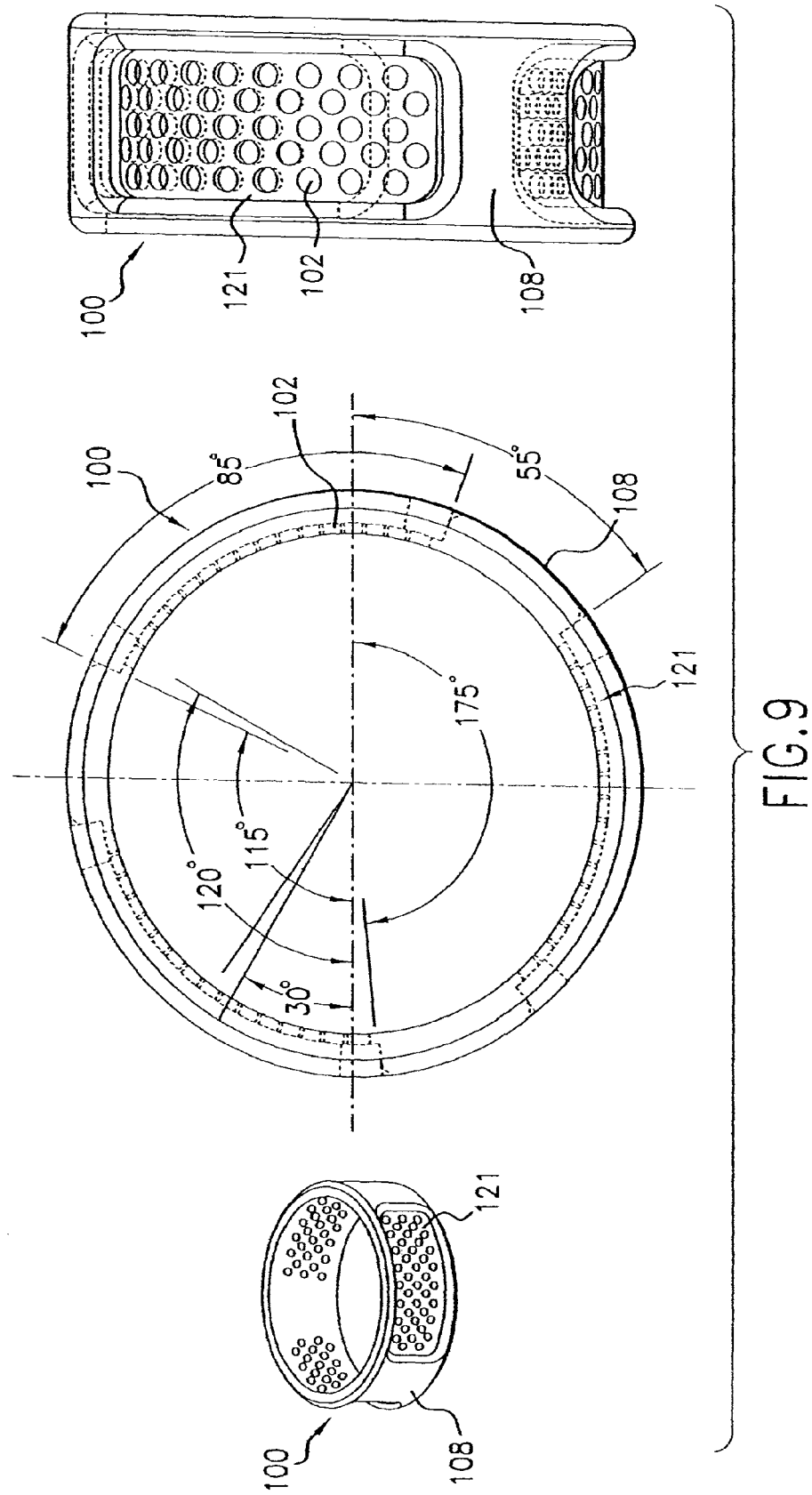
FIG. 9 is a front, perspective and side view of a third embodiment of a suction ring according to the invention.

In a different embodiment, portions of suction ring 100 having holes 102 can be recessed with respect to the rest of the outer surface 104 of suction ring 100. For example, as shown in FIG. 9, recessed portions 121 have a plurality of holes 102 to apply suction to the surrounding tissue. The remaining sectors 108 are not perforated. The purpose of this design is to obtain a configuration of the suction holes 102 that increases traction by drawing portions of the body tissue in recessed portions 121. As the previous configurations, the recessed pattern of FIG. 9 could be made with different size holes, and could encompass different portions of suction ring 100.

Figure 10:
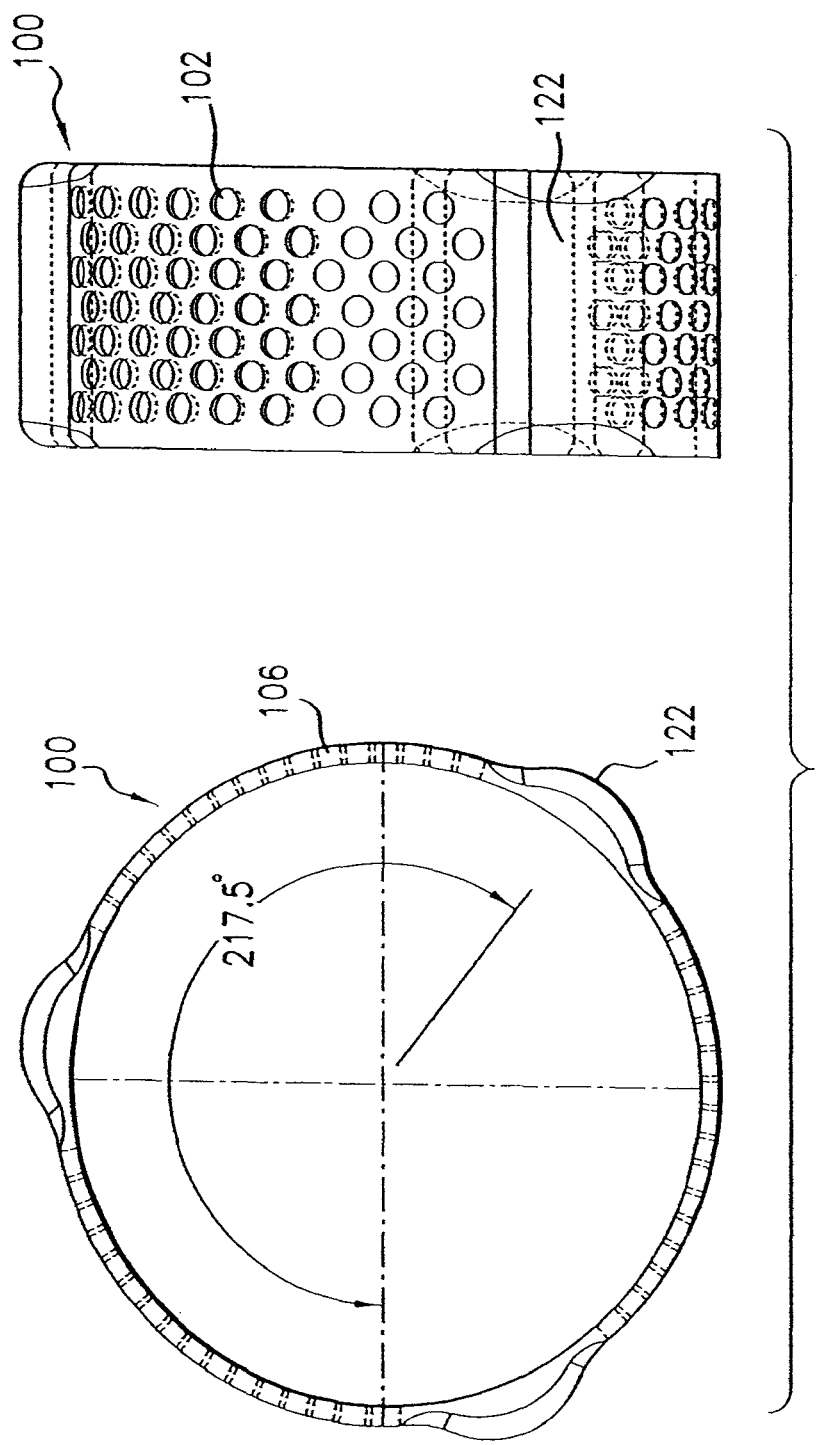
FIG. 10 is a front and side view of a fourth embodiment of a suction ring according to the invention.

FIG. 10 shows a configuration of suction ring 100 that is especially advantageous when the body cavity is inflated with a gas, to facilitate visual inspection and passage of medical instruments. When a gas is forced in the cavity, such as the colon, it passes around the catheter, and tends to detach portions of the outer surface of suction ring 100 from the surrounding tissue. If a portion of perforated suction ring 100 is detached, the rest of suction ring 100 also is likely to become detached from the tissue, especially if outer surface 104 is uniformly perforated. Axial ridges 122 assist in the formation of folds in the tissue surrounding the suction ring 100. The gas forced past suction ring 100 can thus flow in a passage formed by the tissue folds, so that sectors 106 remain attached and keep the suction ring 100 in place.

FIG. 20 shows another design that allows passage of gases forced through the cavity. Suction ring 100 includes perforated sectors 106 separated by grooves 160. Grooves 160 provide a channel for flowing gases, while perforated sectors 106 remain attached to the surrounding tissue.

Figure 11:
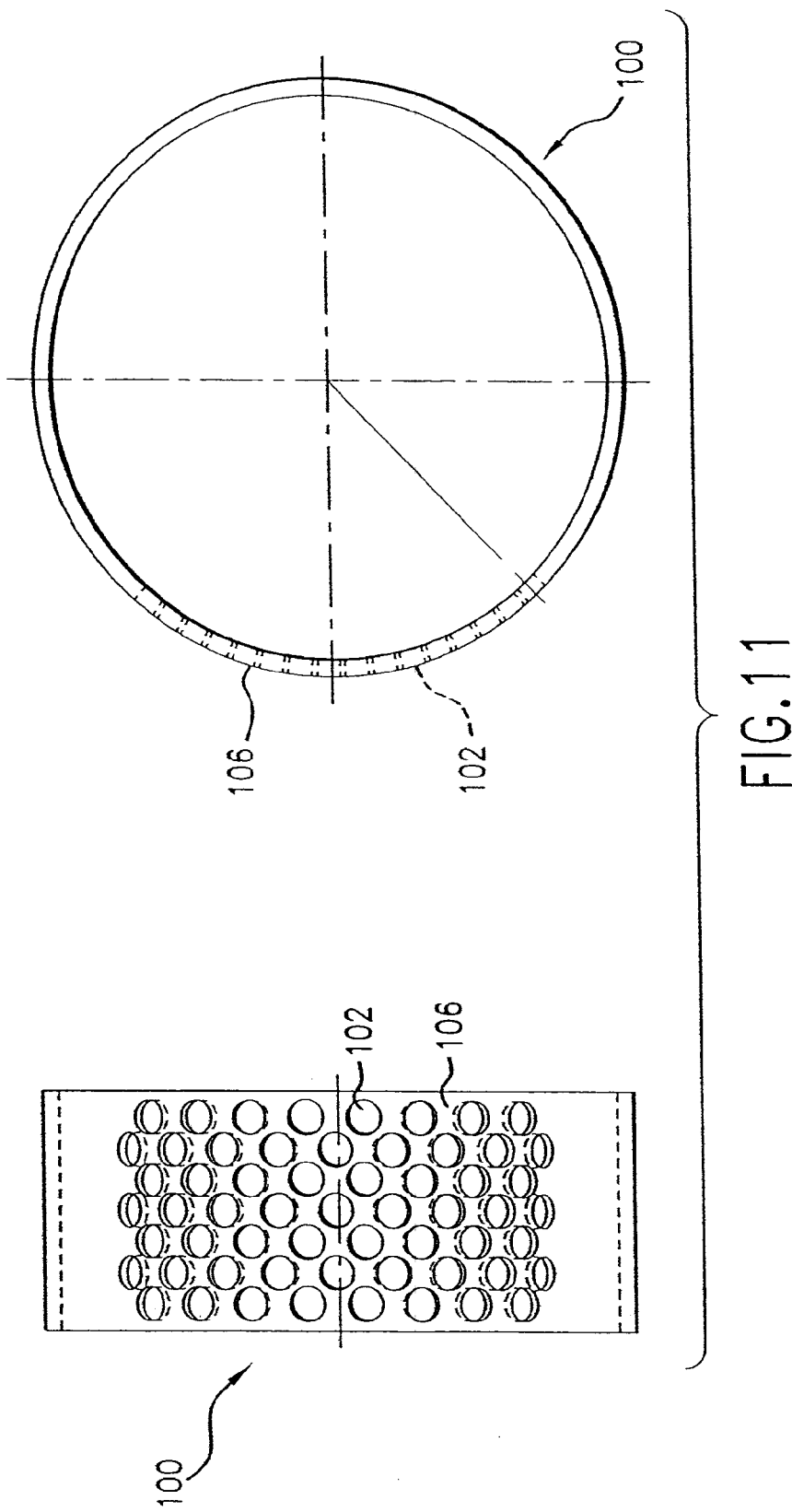
FIG. 11 is a front and side view of a fifth embodiment of a suction ring according to the invention.
Figure 12:
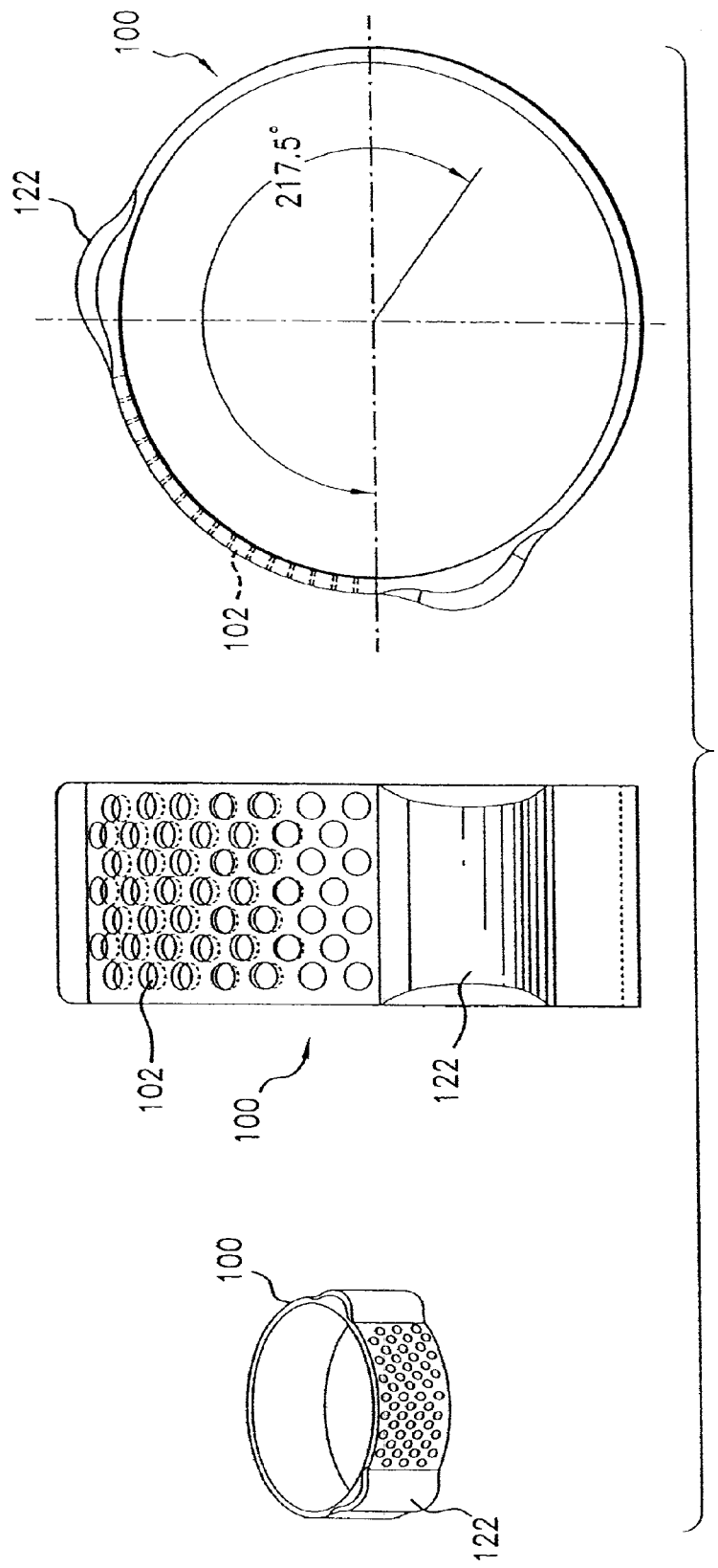
FIG. 12 is a front, perspective and side view of a sixth embodiment of a suction ring according to the invention.

In certain applications, it may be desirable to apply suction to only a portion of the circumference of suction ring 100. FIG. 11 shows one example of such application, where a perforated sector 106 extends over an arc of approximately 85 deg., and the rest of suction ring 100 is not perforated. As described above, the pattern and size of holes 102 can be optimized as desired. In addition, various features also described above can be included in this design, such as axial ridges 122 shown in FIG. 12, and a recessed construction of perforated sector 106, shown in FIG. 13. As before, the purpose of these features is to maximize traction and prevent separation of the entire suction ring 100 from the body cavity tissue.

Figure 14:
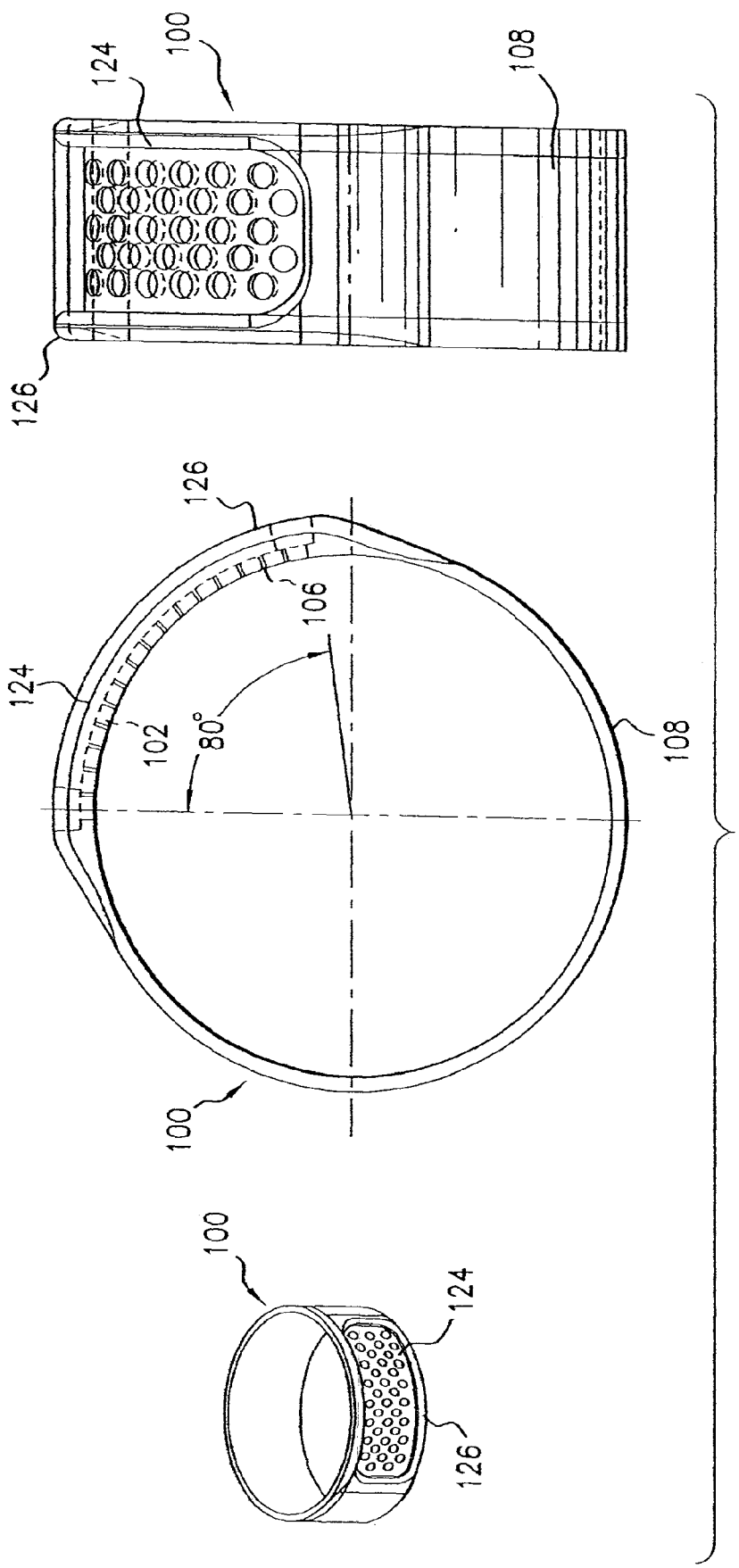
FIG. 14 is a front, perspective and side view of an eighth embodiment of a suction ring according to the invention.

FIG. 14 shows a further embodiment of the suction ring 100, where the perforated sector 106 is recessed, and is further surrounded by peripheral ridges 126. Peripheral ridges 126 are disposed around the recess 124, and protrude above the outer surface 104 of suction ring 100. Peripheral ridges 126 act as a seal that separates the portion of cavity tissue on which perforated sector 106 applies a suction, and the rest of the cavity tissue. In this manner, fluids can flow through the body cavity while the catheter 2 is inserted in the body cavity. The flow can pass between the non perforated sectors 108 of suction ring 100 and the body tissue, while perforated sector 106 together with peripheral ridges 126 maintains a suction against the tissue, and is thus anchored in place.

Figure 15B:
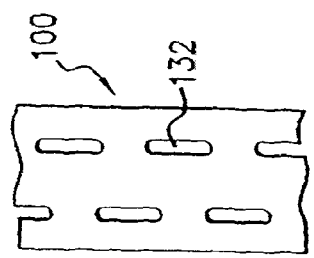
FIG. 15b is a top view of a variation of the embodiment shown in FIG. 15.
Figure 15:
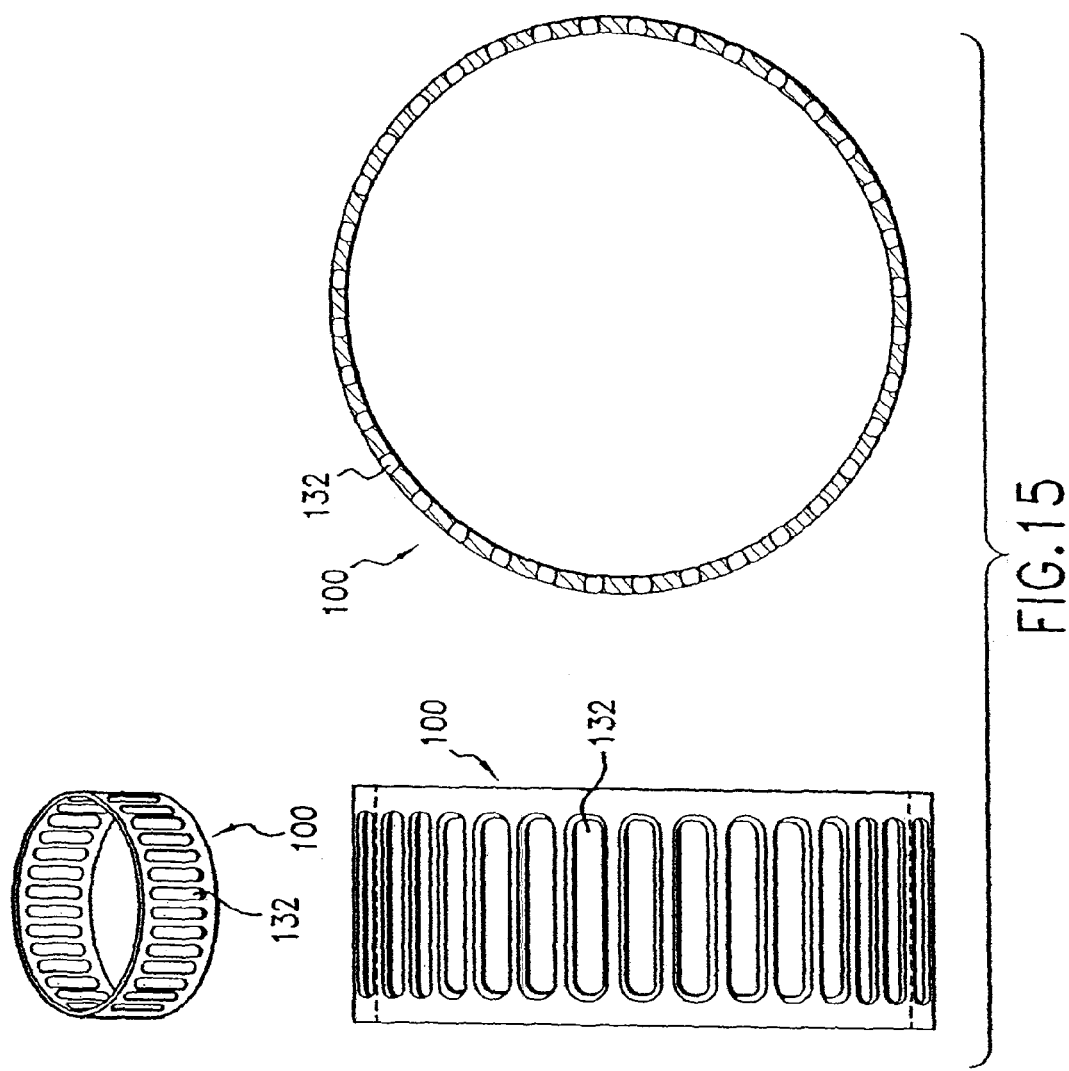
FIG. 15 is a front, perspective and side view of a ninth embodiment of a suction ring according to the invention.

As shown in FIG. 15, suction can be applied to the tissue by slots 132, rather than by round holes 102 described above. Slots 132 can be used with any of the configurations described, and can be disposed perpendicular to the relative motion of catheter 2, as shown in FIG. 15b.

The several configurations of suction ring 100 are especially well suited for use in conjunction with the proximal and distal gripper portions 54,56 shown in FIG. 3. However, the same configurations can also be successfully utilized to maximize the traction generated by gripping pads 24 shown in FIG. 1.

The traction force that can be generated by the propulsion sections of catheter 2 can be increased by increasing the folds and undulations of the cavity tissue in contact with the suction ring 100, thus generating an interference between the tissue of the inner surface of the body cavity and fixed protrusions of the gripping pads 24, 58. For example, suction can be used to draw some tissue in holes, slots or between protrusions formed on suction ring 100. Folds in the tissue then interact with the edges of these structures to generate a force opposing the relative motion between the tissue and suction ring 100 greater than would be possible if the two were simply sliding past each other.

FIG. 16 shows one possible exemplary embodiment utilizing this principle. Tissue 200 of the inner surface of a body cavity is partially drawn inside hole 102 formed in perforated sector 106 of suction ring 100. As suction ring 100 mounted on catheter 2 is moved in a relative direction A, a force $F_A$ resisting the relative motion is applied by the portion of tissue 200 that is drawn by suction inside hole 102. To further increase this traction force, means can be employed to urge the portion of tissue 200 drawn within hole 102 against the perimeter of hole 102. For example, inflatable parts 150 could be inflated, as shown by dashed line 152, to hold tissue 200.

In a different embodiment shown in FIG. 16b, after being drawn inside hole 102, tissue 200 can be trapped between a sleeve 153 and the perimeter of hole 102. For example, sleeve 153 can be concentric with the suction ring 100, and be rotatable or translatable just inside of outer surface 104.

Figure 17:
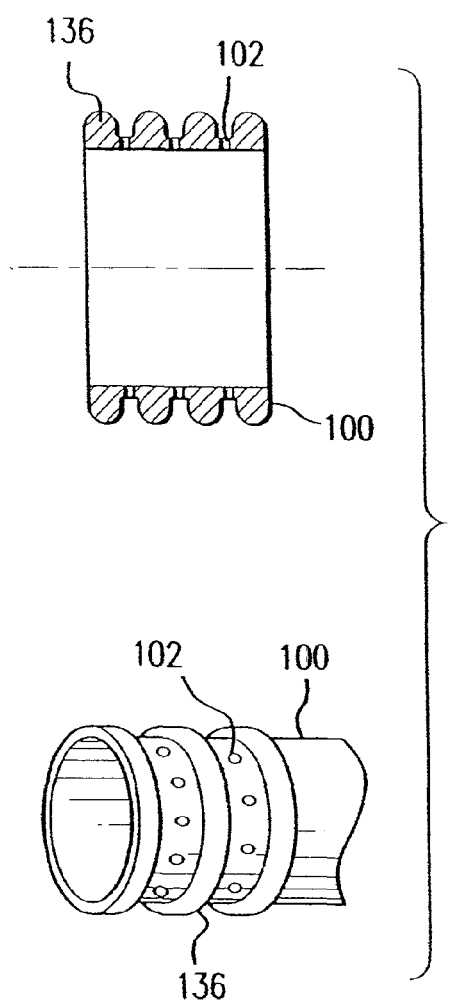
FIG. 17 is a top and perspective view of a tenth embodiment of a suction ring according to the invention.
Figure 18:
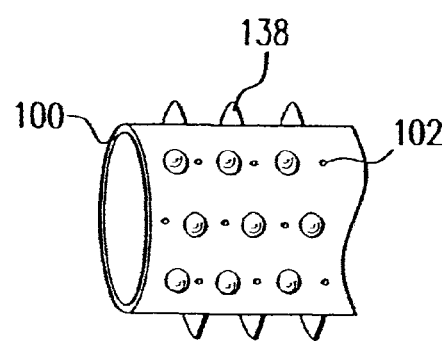
FIG. 18 is a top view of an eleventh embodiment of a suction ring according to the invention.

A different exemplary embodiment of a design to increase traction forces is shown in FIGS. 17 and 18. In this case, protrusions extend from the surface of suction ring 100 to interact with the tissue that is drawn between the protrusions by suction. As shown in FIG. 17, the protrusions can be, for example, ridges 136 disposed in a substantially circumferential direction around suction ring 100. Suction holes 102 can be disposed between the ridges 136, or even on the raised sides of the ridges 136. Instead of ridges, suction ring 100 can have a "soap dish" surface construction, where a plurality of studs 138 extend from the outer surface, and are interspersed with suction holes 102. This embodiment is shown in FIG. 18.

To maximize the resistance to relative movement between the catheter and the tissue, the studs can be staggered in the direction of relative movement. The designs shown in FIGS. 17 and 18 take advantage of the same mechanism described with reference to FIG. 16.

Figure 21A:
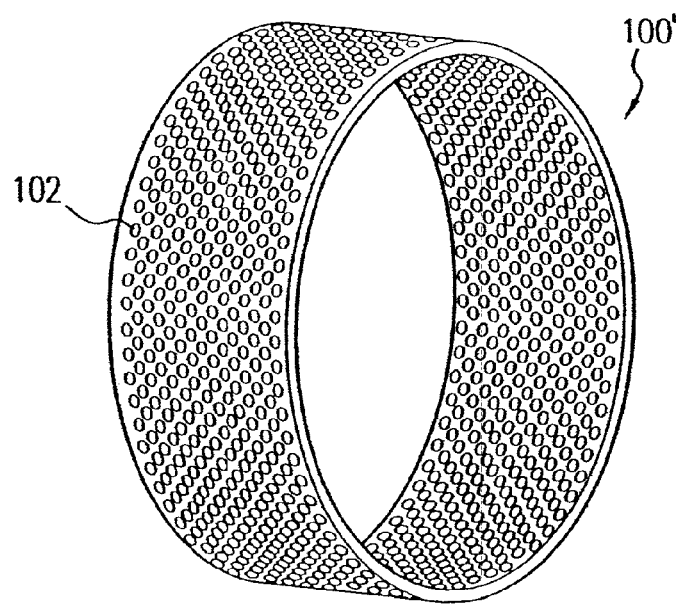
FIG. 21a is a perspective view of a thirteenth embodiment of a suction ring according to the invention.
Figure 21B:
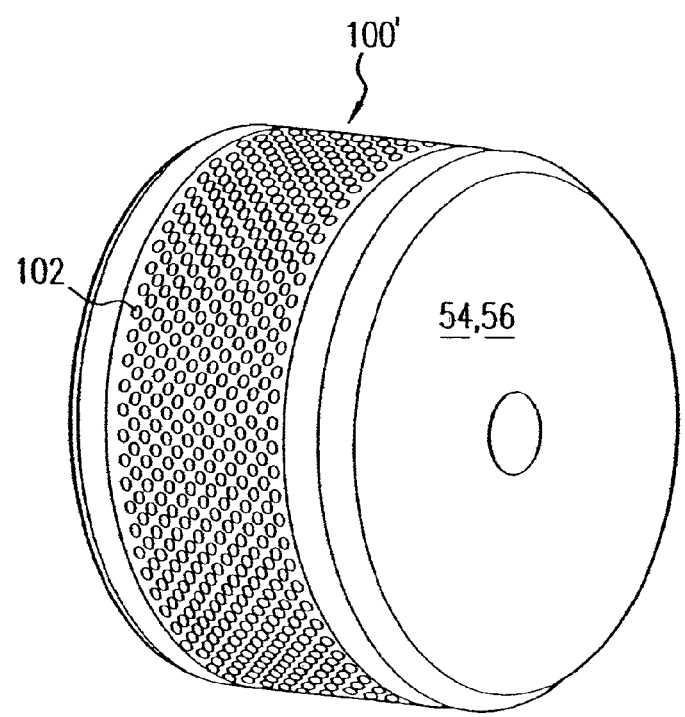
FIG. 21b is a perspective view of a fourteenth embodiment of a suction ring according to the invention.

The force exerted by gripper portions 54, 56 can also be varied by changing the axial length of suction ring 100, and the number of rows of holes 102. For example, FIG. 21a shows a suction ring 100' having two additional rows of holes 102, in the axial direction of the catheter. FIG. 21b shows the same suction ring 100' used in a gripper portion 54, 56, to generate a greater force.

An example of how the catheter introducer system according to the invention can be used will now be described with reference to FIGS. 1 through 3. A common procedure in endoscopy is the examination of the colon and removal of polyps present in the colon. A vision light tool (VLT) is inserted into the steering catheter 2 and is secured to the end of the catheter 2. Catheter 2 is then inserted into the rectum using a rigid sheath 20. The catheter 2 is then driven through the intestine towards the cecum while being guided and controlled by a control unit 34. In one embodiment according to the invention, control unit 34 includes a monitor through which the operator can view what is being transmitted by the VLT, so that he can drive the catheter forward or backwards while simultaneously steering it. During tests, the propulsion section was able to resist a pulling force of approximately 2.5 lbs. while remaining attached in position in a colon by suction.

After reaching the cecum, the device is then slowly pulled back from the cecum to the rectum, as the interior of the intestine is inspected. When a polyp is sighted, a suction polypectomy device is inserted into the catheter until it protrudes from the distal end 4 of catheter 2, and is seen on the monitor by the operator. The suction polypectomy tool is steered to the polyp, and the polyp is excised and withdrawn by vacuum through the suction channel of the polypectomy tool. Additional tools can be introduced and brought into position at the site of interest rapidly and easily through working channel 10, because catheter 2 maintains access to the operation site while various tools are withdrawn and inserted back into the catheter.

In a preferred embodiment according to the invention, the various diagnostic and therapeutic tools used in endoscopy are positioned accurately with respect to the body cavity by moving the distal end 4 of the catheter 2 with the steering section 36, or with the steering/propulsion section 50. In a different embodiment, still within the scope of the invention, the endoscopic tools can be positioned accurately by using a separate positioning system, which could include push-pull wires 38 similar to those shown in FIG. 2, or a system including inflatable bellows, linear actuators, or a combination of these devices. Also in a preferred embodiment according to the invention, many components of the catheter introducer system are disposable, thus assuring a high degree of sterility to the device. For example, the flexible tube of catheter 2 can be disposable, as well as various portions of the endoscope tools 8 used within working channel 10.

As indicated, the catheter introducer system of the present invention could be used to navigate within body cavities other than the GI tract. For example, air passages or blood vessels could be explored using this system. For blood vessels, it would be necessary to reduce the size of the apparatus, and preferably to only use the steering section, to avoid interference with blood flow through the vessel. For example, an outer diameter of the device would have to be less than about 2 mm.

It will be apparent to those skilled in the art that various modifications and variations can be made in the structure and the methodology of the present invention, without departing from the spirit or scope of the invention. Thus, it is intended that the present invention cover the modifications and variations of this invention provided they come within the scope of the appended claims and their equivalents.

What is claimed is:

1. A system for exploring a body cavity, the system comprising:
   a flexible catheter having a length extending from a distal end for introduction in the cavity to a proximal end opposite the distal end;
   a channel within the catheter, adapted for guiding a medical tool along the length of the catheter;
   a propulsion section of the catheter disposed adjacent the distal end, adapted for pulling the catheter through the cavity, wherein the propulsion section comprises:
      a distal gripper portion attached to the catheter at an axial position that is fixed relative to the distal end of the catheter, wherein the distal gripper portion is adapted for selectively gripping by suction and releasing tissue of an inner portion of the cavity; and
      a proximal gripper portion attached to the catheter at an axial position disposed further from the distal end than the distal gripper portion, and fixed relative to the proximal end of the catheter, wherein the proximal gripper portion is adapted for selectively gripping by suction and releasing the tissue of the cavity;
      wherein each of the proximal and distal gripper portions comprises a suction ring having an outer surface defining a plurality of suction holes, the suction ring extending circumferentially around the catheter;
      wherein each suction ring comprises at least one perforated sector comprising the suction holes and at least one non-perforated sector; and
      wherein at least one suction ring includes a perforated sector that is recessed relative to the outer surface of the suction ring; and
   a steering section of the catheter disposed adjacent the distal end, wherein the steering section is configured to extend and contract axially so as to move, adapted for pointing the distal end in a desired direction.

2. The system according to claim 1, wherein the at least one perforated sector extends over a first portion of the circumference of the suction ring, and the at least one non-perforated sector extends over a second portion of the circumference of the suction ring, such that the suction holes are not uniformly distributed around the circumference of the suction ring.

3. The system according to claim 1, wherein the suction holes have a diameter of between approximately 0.02" and 0.04".

4. The system according to claim 1, wherein at least one perforated sector comprises at least two perforated sectors.

5. The system according to claim 1, wherein at least one of the suction rings further comprises axial ridges separating the at least one perforated sector and the at least one non-perforated sector.

6. The system according to claim 1, further comprising a plenum disposed radially inside the outer surface of the suction ring.

7. The system according to claim 1, wherein the steering section comprises control wires attached to the distal gripper portion, the control wires being each independently extendable and retractable.

8. The system according to claim 7, further comprising sutures securing the control wires to a flexible structure.

9. The system according to claim 1, further comprising a control unit configured to provide suction to the proximal and distal gripper portions, and to extend and contract the steering section.

10. The system according to claim 1, further comprising a rigid sheath disposed around the catheter, slidable along a length of the catheter.

11. A system for exploring a body cavity, the system comprising:
   a flexible catheter having a length extending from a distal end for introduction in the cavity to a proximal end opposite the distal end;
   a channel within the catheter, adapted for guiding a medical tool along the length of the catheter;
   a propulsion section of the catheter disposed adjacent the distal end, adapted for pulling the catheter through the cavity, wherein the propulsion section comprises:
      a distal gripper portion attached to the catheter at an axial position that is fixed relative to the distal end of the catheter, wherein the distal gripper portion is adapted for selectively gripping by suction and releasing tissue of an inner portion of the cavity; and
      a proximal gripper portion attached to the catheter at an axial position disposed further from the distal end than the distal gripper portion, and fixed relative to the proximal end of the catheter, wherein the proximal gripper portion is adapted for selectively gripping by suction and releasing the tissue of the cavity;
      wherein each of the proximal and distal gripper portions comprises a suction ring having an outer surface defining a plurality of suction holes, the suction ring extending circumferentially around the catheter;
      wherein each suction ring comprises at least one perforated sector comprising the suction holes and at least one non-perforated sector; and
      wherein at least one suction ring includes a peripheral ridge extending above the outer surface of the suction ring, surrounding the at least one perforated sector; and
   a steering section of the catheter disposed adjacent the distal end, wherein the steering section is configured to extend and contract axially so as to move, adapted for pointing the distal end in a desired direction.

12. The system according to claim 11, wherein the at least one perforated sector extends over a first portion of the circumference of the suction ring, and the at least one non-perforated sector extends over a second portion of the circumference of the suction ring, such that the suction holes are not uniformly distributed around the circumference of the suction ring.

13. The system according to claim 11, comprising at least two perforated sectors.

14. The system according to claim 13, comprising at least two peripheral ridges surrounding each of the at least two perforated sectors.

15. The system according to claim 11, further comprising a plenum disposed radially inside the outer surface of the suction ring.

16. A system for exploring a body cavity, the system comprising:
   a flexible catheter having a length extending from a distal end for introduction in the cavity to a proximal end opposite the distal end;
   a channel within the catheter, adapted for guiding a medical tool along the length of the catheter;

a propulsion section of the catheter disposed adjacent the distal end, adapted for pulling the catheter through the cavity, wherein the propulsion section comprises:

a distal gripper portion attached to the catheter at an axial position that is fixed relative to the distal end of the catheter, wherein the distal gripper portion is adapted for selectively tissue of an inner portion of the cavity; and a proximal gripper portion attached to the catheter at an axial position disposed further from the distal end than the distal gripper portion, and fixed relative to the proximal end of the catheter, wherein the proximal gripper portion is adapted for selectively gripping by suction and releasing the tissue of the cavity;

wherein each of the proximal and distal gripper portions comprises a suction ring having an outer surface defining a plurality of suction holes, the suction ring extending circumferentially around the catheter; and wherein each suction ring comprises at least one perforated sector comprising the suction holes and at least one non-perforated sector;

a steering section of the catheter disposed adjacent the distal end, wherein the steering section is configured to extend and contract axially so as to move, adapted for pointing the distal end in a desired direction; and at least one inflatable member for urging the tissue of the cavity against a perimeter of the suction holes.

17. The system according to claim 16, comprising at least two inflatable members.

18. The system according to claim 16, wherein the at least one inflatable member is disposed substantially perpendicular to a longitudinal axis of the catheter.

19. The system according to claim 16, wherein the at least one inflatable member is disposed adjacent to a suction hole.

20. The system according to claim 16, wherein the at least one perforated sector of at least one of the suction rings includes the at least one inflatable member.

* * * * *

UNITED STATES PATENT AND TRADEMARK OFFICE
CERTIFICATE OF CORRECTION

PATENT NO. : 8,602,973 B2
APPLICATION NO. : 12/567376
DATED : December 10, 2013
INVENTOR(S) : Jeffrey Michael Wendlandt Page 1 of 1

It is certified that error appears in the above-identified patent and that said Letters Patent is hereby corrected as shown below:

In the Claims:

In claim 16, col. 17, line 7, "selectively tissue" should read --selectively gripping by suction and releasing tissue--.

Signed and Sealed this
Twenty-ninth Day of July, 2014

Michelle K. Lee
*Deputy Director of the United States Patent and Trademark Office*